(12) United States Patent
Karazivan et al.

(10) Patent No.: US 8,721,327 B2
(45) Date of Patent: *May 13, 2014

(54) SYSTEM AND METHOD FOR DETECTION AND REMOVAL OF DENTAL TARTAR

(75) Inventors: Naim Karazivan, Montreal (CA); Emmanuel Montini, Ste-Anne-des-Lacs (CA); François Ayotte, Laval (CA)

(73) Assignee: Dentsply Canada Ltd., Woodbridge, ON (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/091,099

(22) Filed: Apr. 20, 2011

(65) Prior Publication Data

US 2011/0294089 A1     Dec. 1, 2011

Related U.S. Application Data

(62) Division of application No. 10/471,284, filed as application No. PCT/CA02/00409 on Mar. 21, 2002, now abandoned.

(30) Foreign Application Priority Data

Mar. 21, 2001  (CA) .................................... 2341105

(51) Int. Cl.
*A61C 1/00*     (2006.01)
(52) U.S. Cl.
USPC ........................................................ 433/29
(58) Field of Classification Search
USPC ............... 433/29, 86, 118, 119, 215, 216; 132/309, 311; 356/309, 311, 317, 318, 356/341; 600/410, 411, 476, 477; 385/12, 385/31, 369
See application file for complete search history.

(56) References Cited

U.S. PATENT DOCUMENTS

| 2,437,916 A | 3/1948 | Greenwald |
| 4,184,175 A | 1/1980 | Mullane |

(Continued)

FOREIGN PATENT DOCUMENTS

| DE | 4015066 | 11/1991 |
| DE | G9317984 | 5/1995 |

(Continued)

OTHER PUBLICATIONS

Examination Report of Apr. 27, 2006 for European patent application No. 02 708 093.6.

(Continued)

Primary Examiner — Sunil K Singh
(74) Attorney, Agent, or Firm — Anglehart et al.

(57) ABSTRACT

A dental tartar detection and removal device (10) comprises a powered tartar removal instrument (12) adapted to be displaced along a tooth (T), illumination means (14) for illuminating with an incident light a region on the examined or periodontal site, detection means (16) for collecting the light reflected there at, and an analysing system for providing a signal to an operator (OP) of the tartar removal instrument (12) or to the tartar removal instrument when measurements on the reflected light in one or more predetermined ranges of wavelengths fall within any first predetermined range of values that are characteristic of tartar, or when said measurements do not fall within any second predetermined range of values that are characteristic of artefacts other than tartar. As a result of the signal, the removal instrument becomes actuated, either by the operator (OP) or automatically, and the operator can proceed to removing the detected tartar (S) without having to remove the detection device, whereby detection can be continued while the tartar removal instruments (12) is in a tartar removal position, and until all tartar (S) has been removed.

25 Claims, 21 Drawing Sheets

(56) References Cited

U.S. PATENT DOCUMENTS

| | | | |
|---|---|---|---|
| 4,787,847 A | 11/1988 | Martin et al. |
| 4,790,751 A | 12/1988 | Reinhardt et al. |
| 4,858,001 A | 8/1989 | Milbank et al. |
| 5,230,621 A | 7/1993 | Jacoby |
| 5,306,144 A | 4/1994 | Hibst et al. |
| 5,324,129 A | 6/1994 | Root |
| 5,328,365 A | 7/1994 | Jacoby |
| 5,370,944 A | 12/1994 | Omori et al. |
| 5,381,619 A | 1/1995 | Watkins |
| 5,382,163 A | 1/1995 | Putnam |
| 5,460,316 A | 10/1995 | Hefele |
| 5,527,262 A | 6/1996 | Monroe et al. |
| 5,562,448 A | 10/1996 | Mushabac |
| 5,587,284 A | 12/1996 | Brattesani |
| 5,735,792 A | 4/1998 | Vanden Hoek et al. |
| 5,855,974 A | 1/1999 | Wu et al. |
| 5,880,826 A | 3/1999 | Jung et al. |
| 5,894,620 A | 4/1999 | Polaert et al. |
| 5,961,327 A | 10/1999 | Lohn |
| 6,024,562 A | 2/2000 | Hibst et al. |
| 6,039,565 A | 3/2000 | Chou et al. |
| 6,053,731 A | 4/2000 | Heckenberger |
| 6,095,810 A | 8/2000 | Bianchetti |
| 6,102,704 A | 8/2000 | Eibofner et al. |
| 6,135,774 A | 10/2000 | Hack et al. |
| 6,179,611 B1 | 1/2001 | Everett et al. |
| 6,186,780 B1 | 2/2001 | Hibst et al. |
| 6,402,511 B1 | 6/2002 | Calderwood |
| 6,561,802 B2 | 5/2003 | Alexander |
| 2001/0023057 A1 | 9/2001 | Alexander |

FOREIGN PATENT DOCUMENTS

| | | |
|---|---|---|
| DE | 29704185 | 6/1997 |
| DE | 29705934 | 7/1997 |
| DE | 19742701 A1 | 4/1998 |
| EP | 0326497 | 11/1993 |
| EP | 0914809 | 2/2003 |
| JP | 61-171913 | 10/1986 |
| JP | 07-502441 | 3/1995 |
| JP | 408071092 | 3/1996 |
| JP | 10-314194 | 12/1998 |
| JP | 2000-24013 | 1/2000 |
| WO | WO9312732 | 7/1993 |
| WO | WO9901746 | 1/1999 |
| WO | WO0152723 | 7/2001 |
| WO | WO9959462 | 7/2001 |

OTHER PUBLICATIONS

Examination report of Feb. 14, 2011 for australian patent application No. 2009233653.
Examination report of Feb. 5, 2008 for Australian patent application No. 2007203211.
Examination report of Jun. 29, 2010 for European patent application No. 02 708 093.6.
Examination report of Sep. 15, 2004 for European patent application No. 02 708 093.6.
Fourier Transform Infrared Photoacoustic Spectroscopy of Dental Calculus, Mikrochimi. Acta (Wien) 1988, II, 133-136.
International Preliminary Examination Report of PCT/CA02/00409.
International Search Report of PCT/CA02/00409.
Office action of Apr. 28, 2011 for canadian patent applicaiton No. 2,441,857.
Office action of Jul. 5, 2010 for Canadian patent application No. 2,441,857.
Office action of May 27, 2008 for Japanese patent application No. 2002-572875.
office action of Oct. 23, 2007 for Japanese application No. 2002-572875.
Office action of Sep. 21, 2010 for Japanese patent application No. 2002-572875.

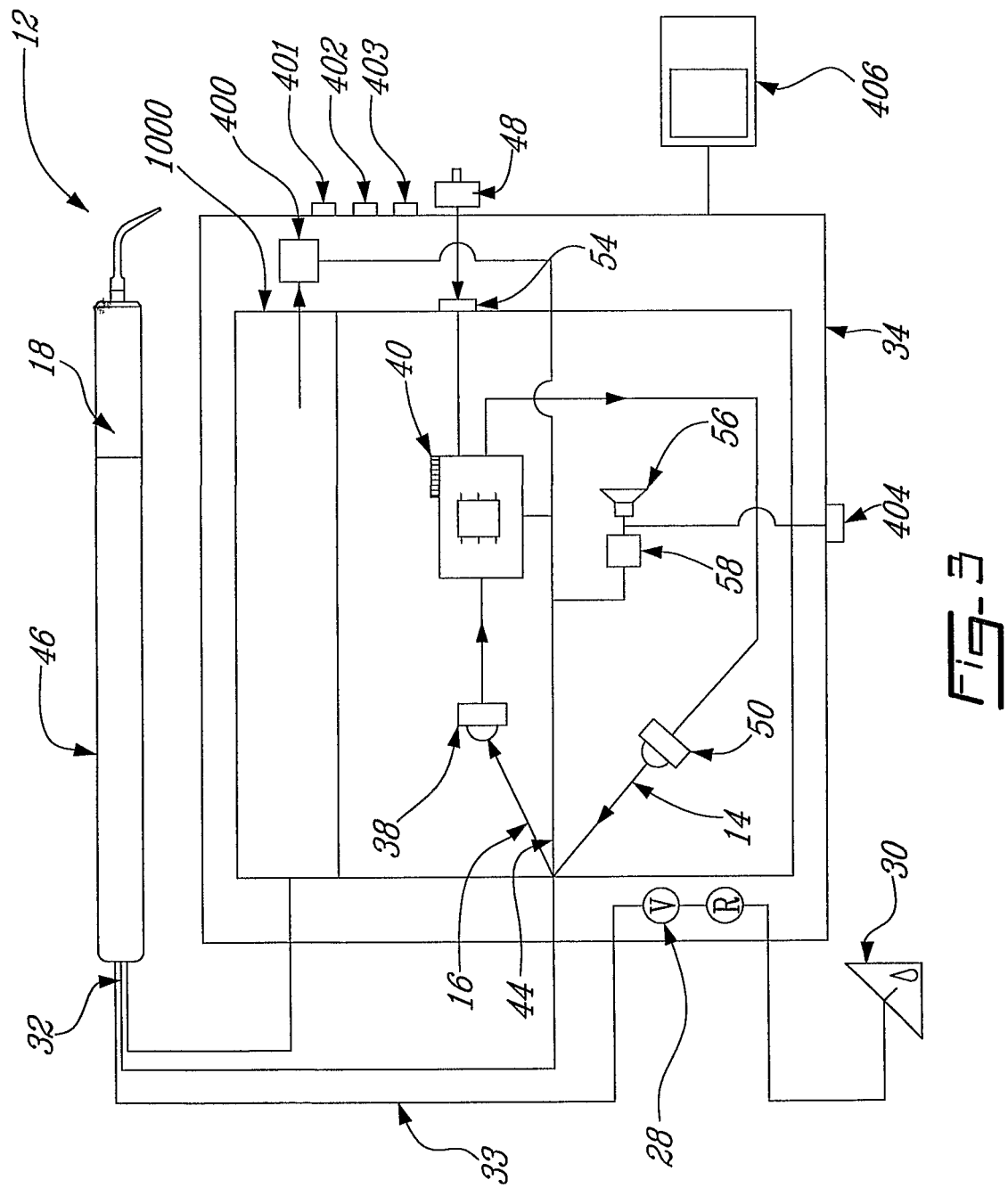

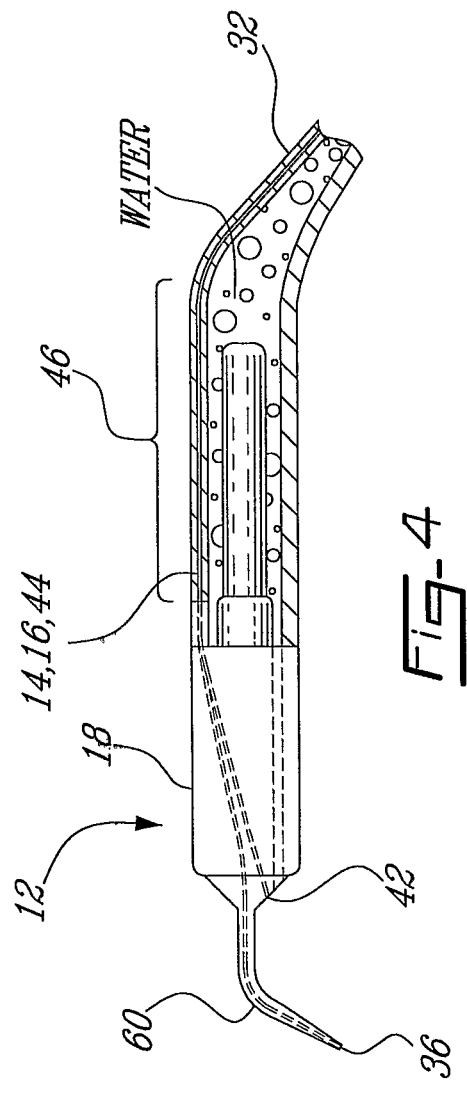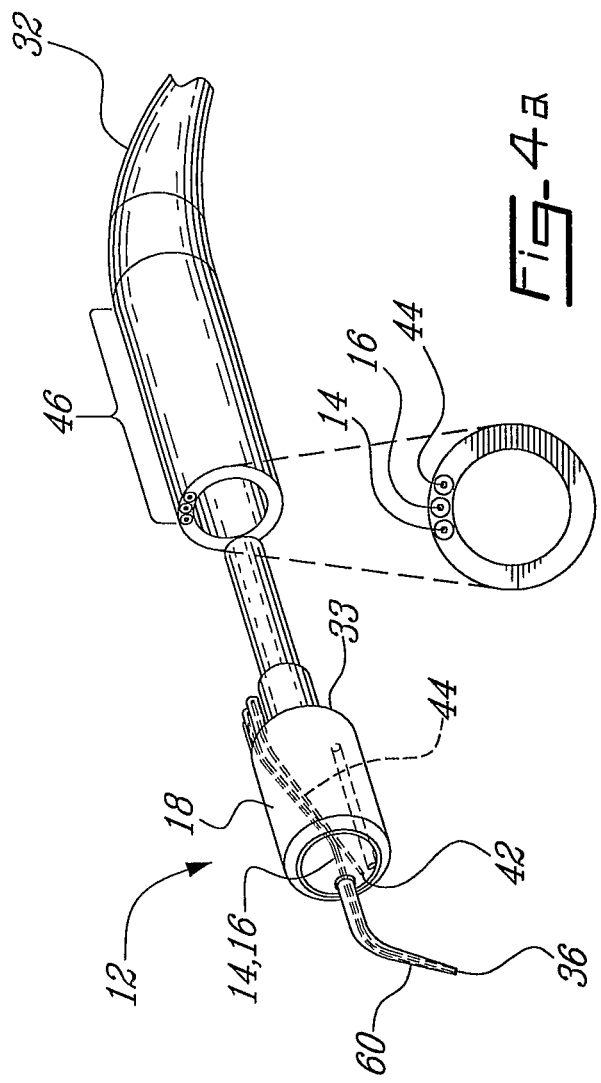

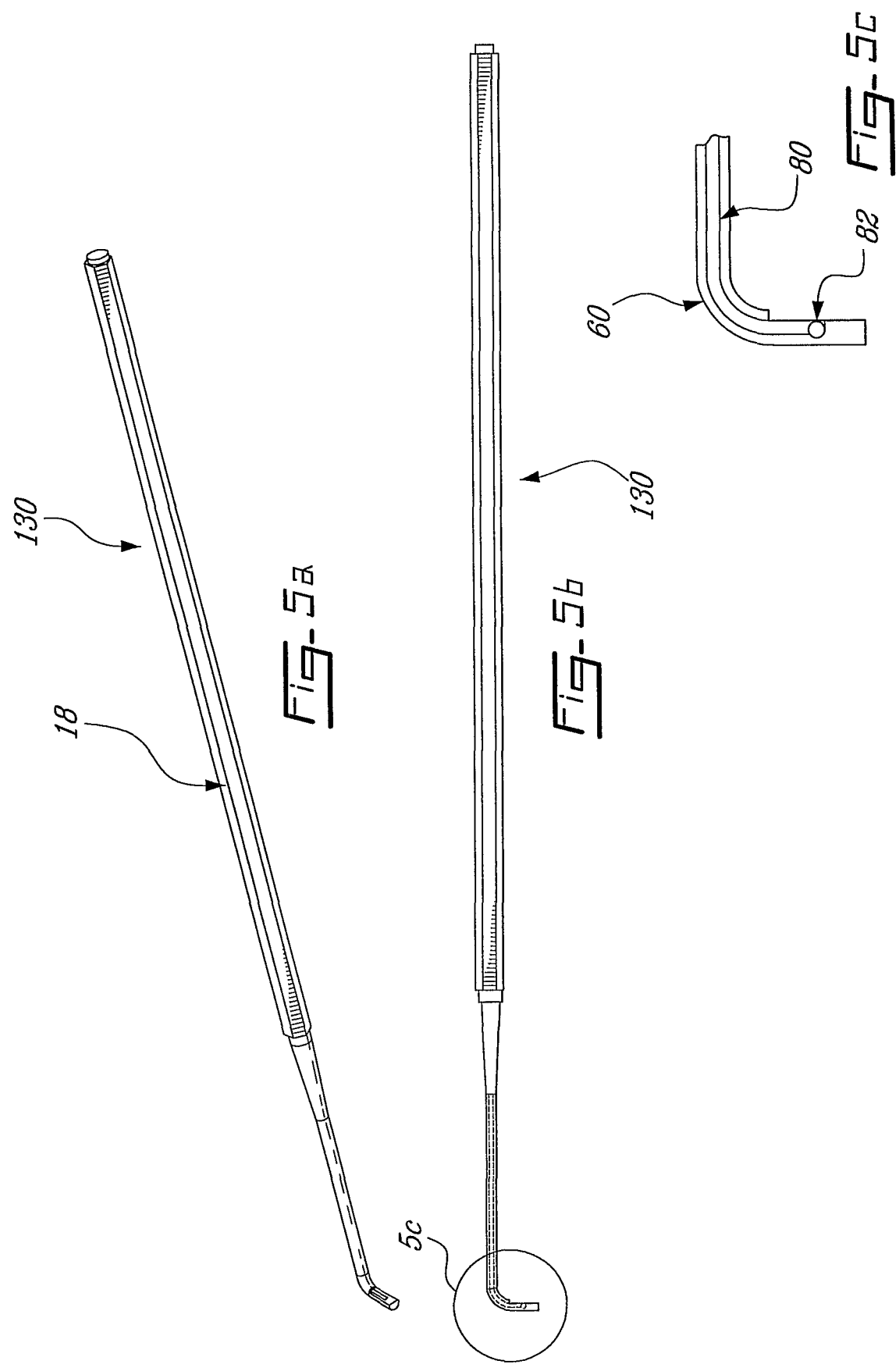

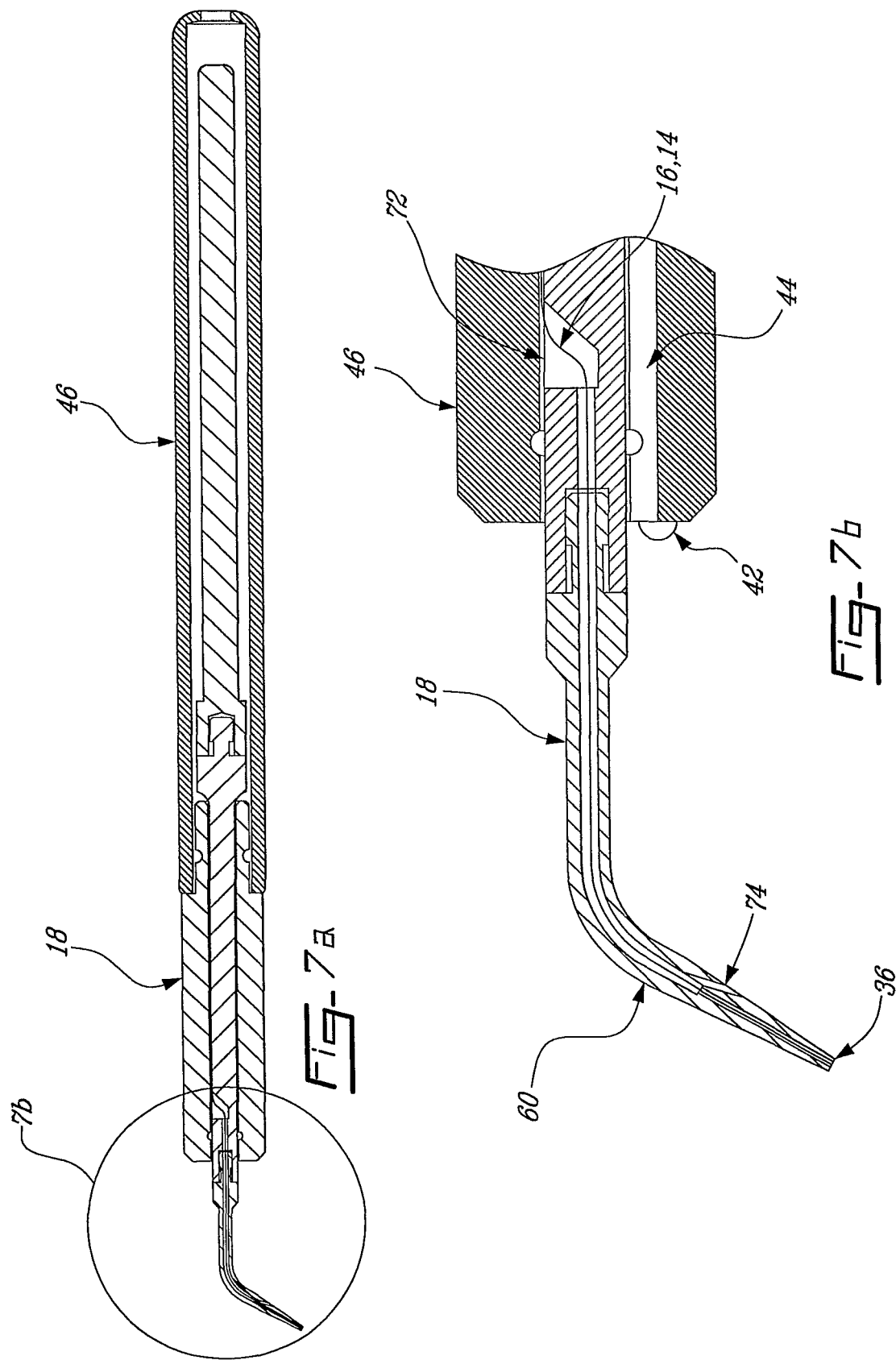

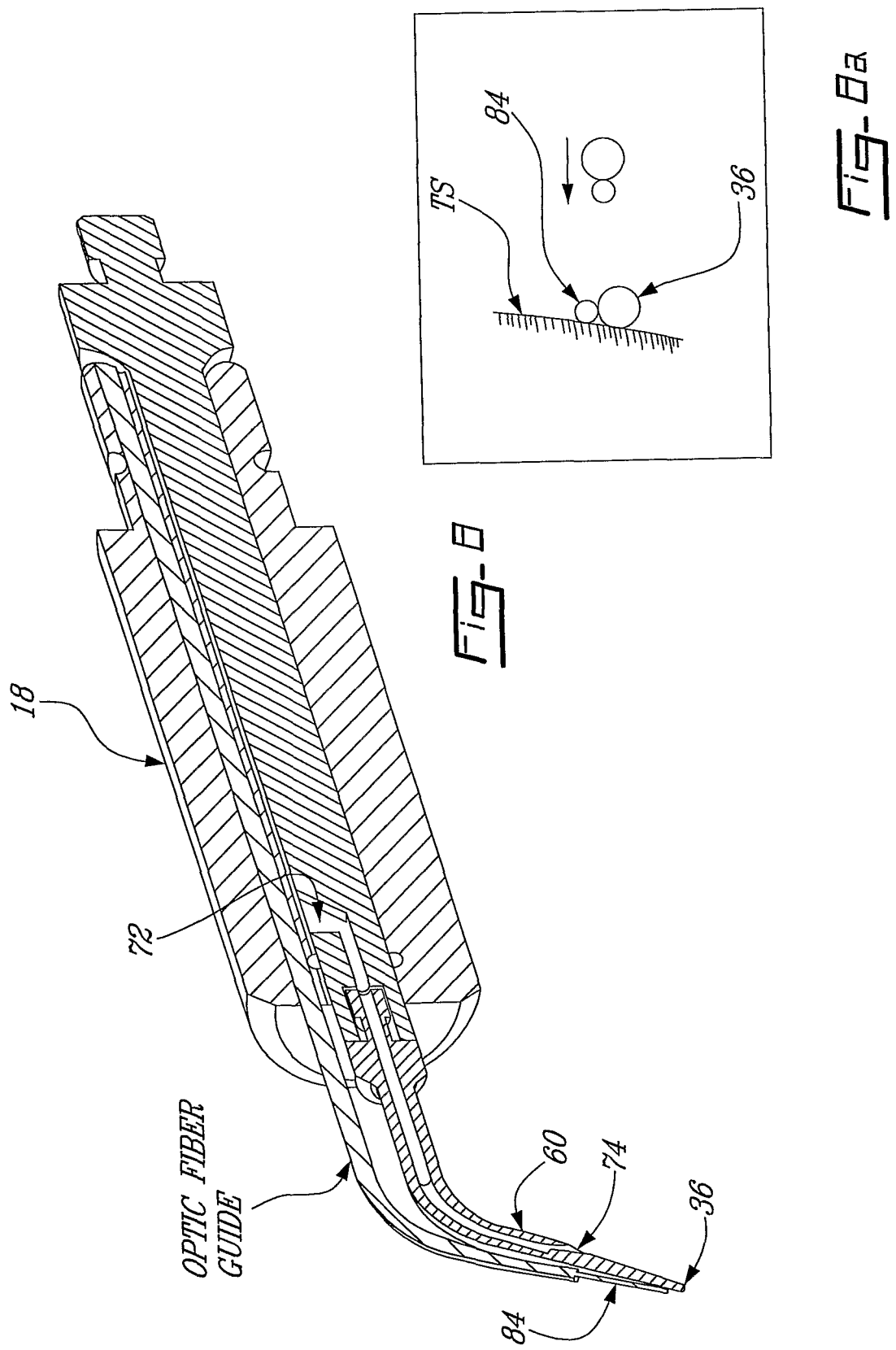

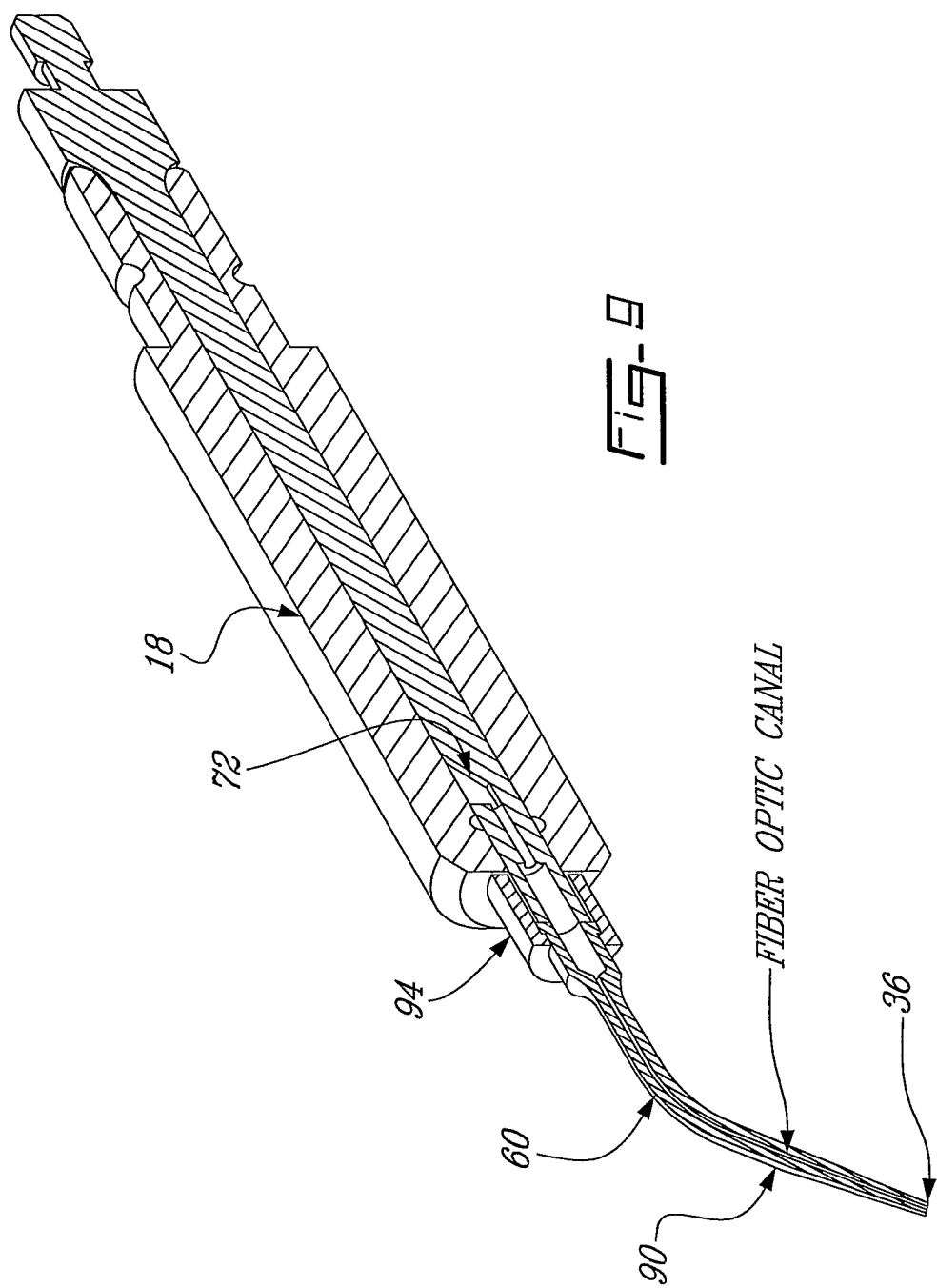

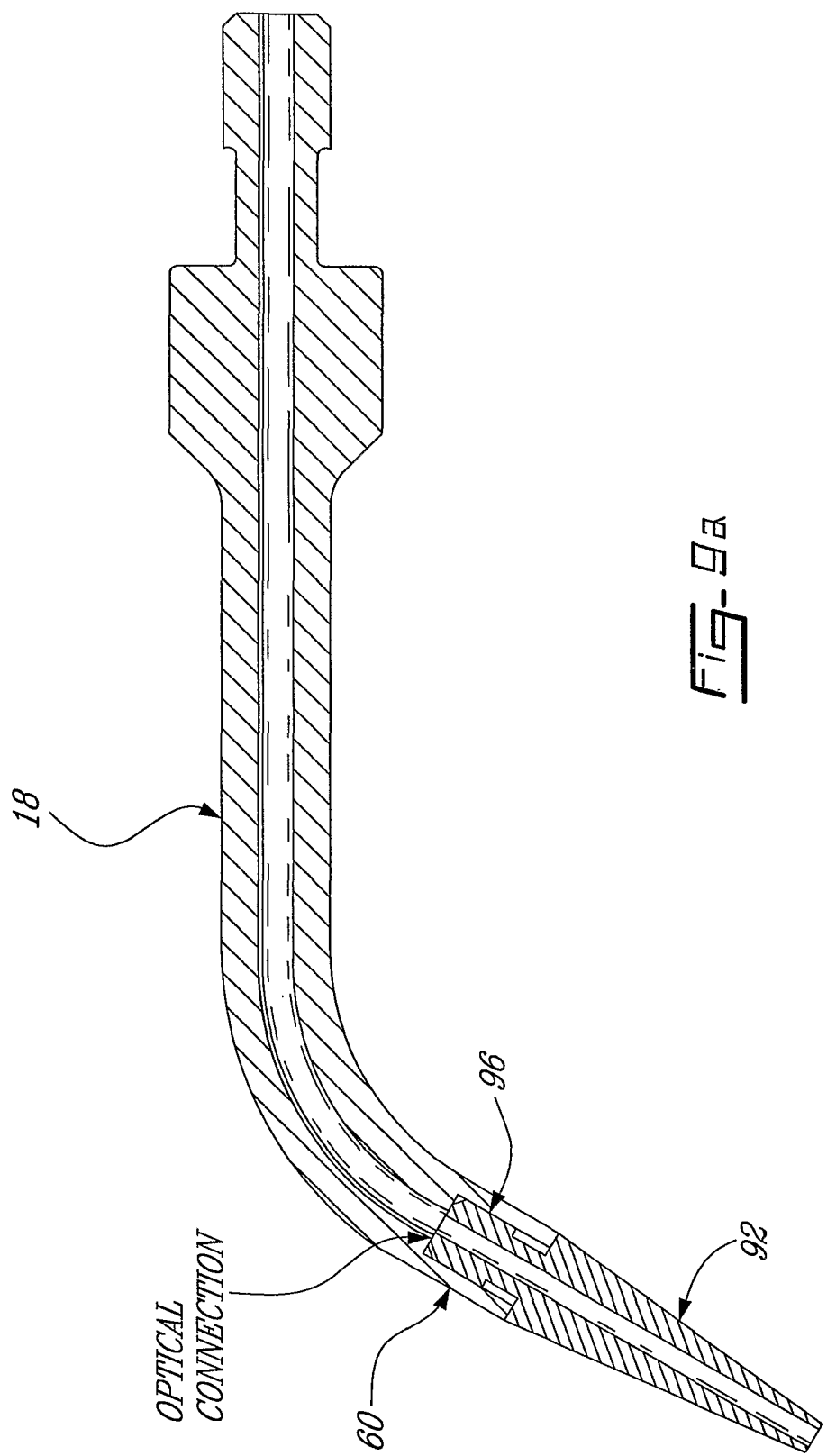

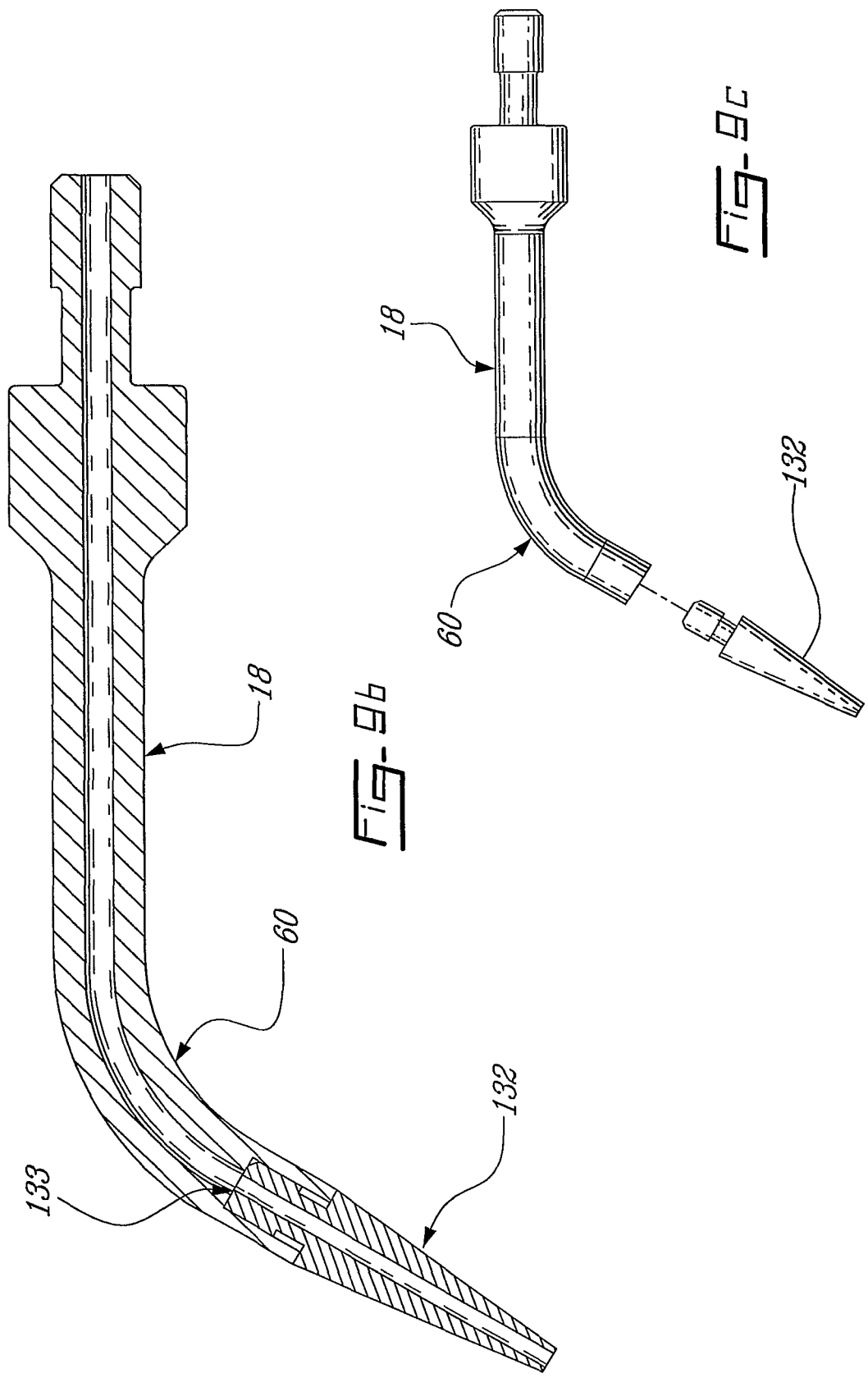

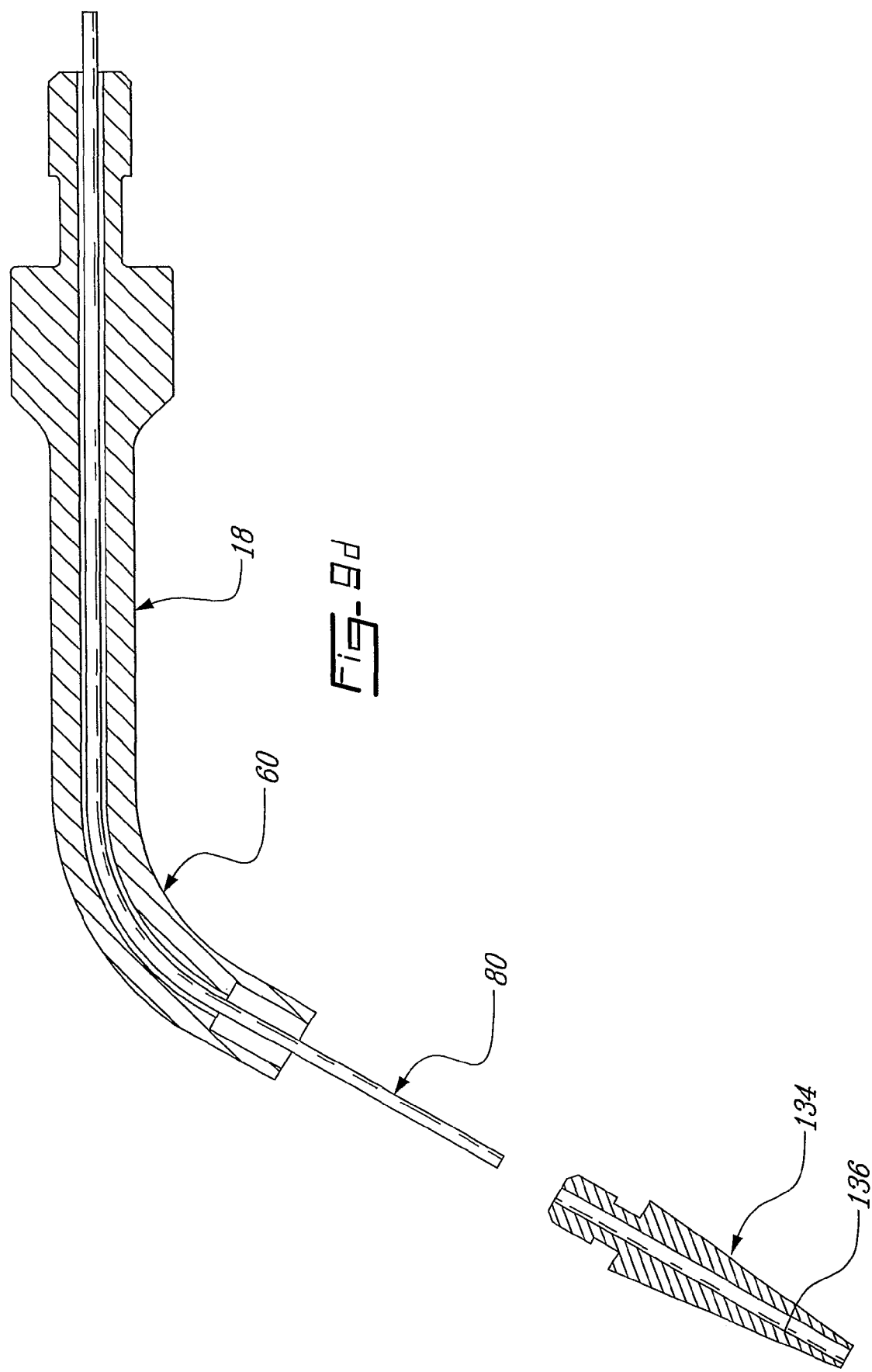

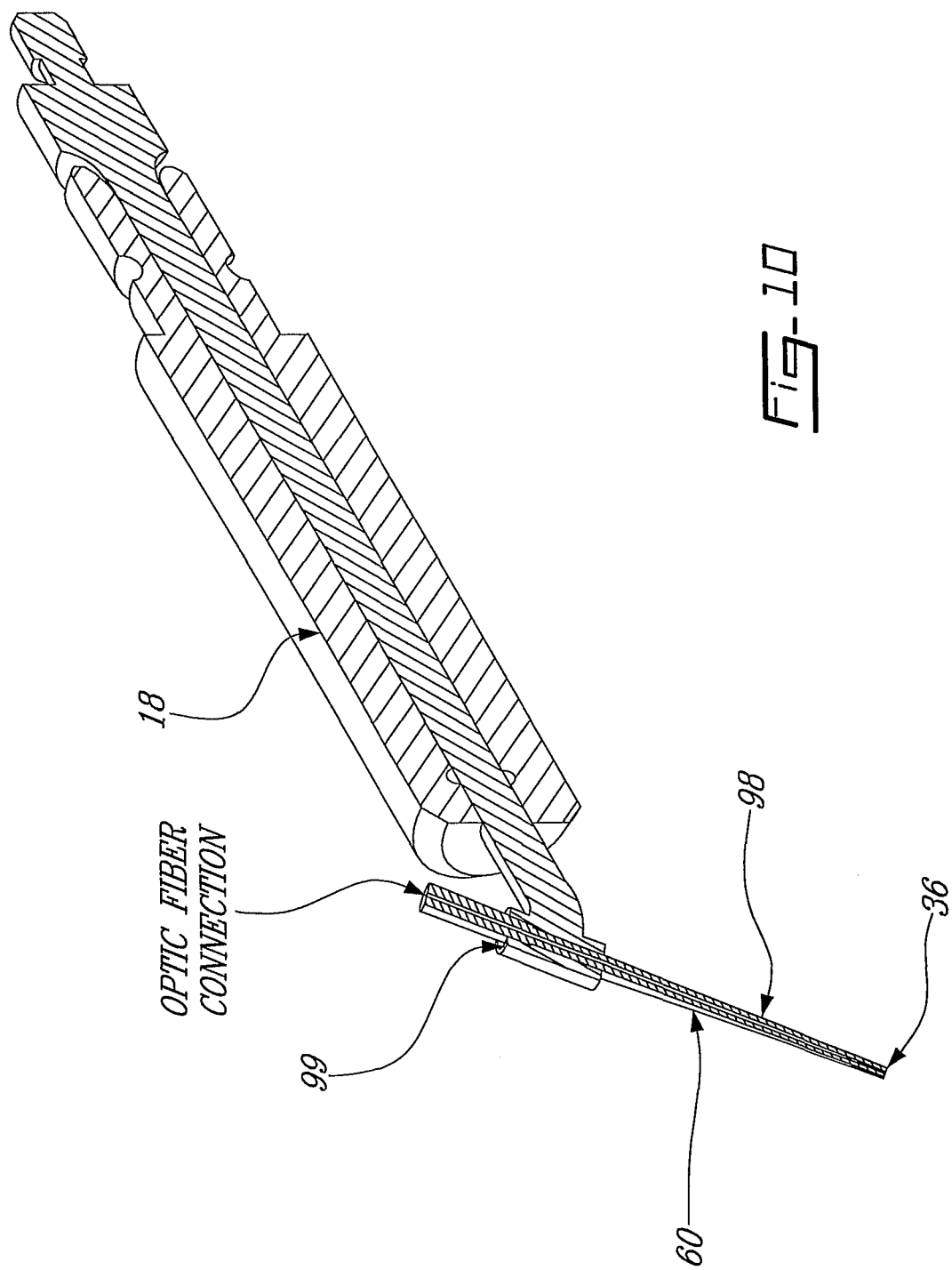

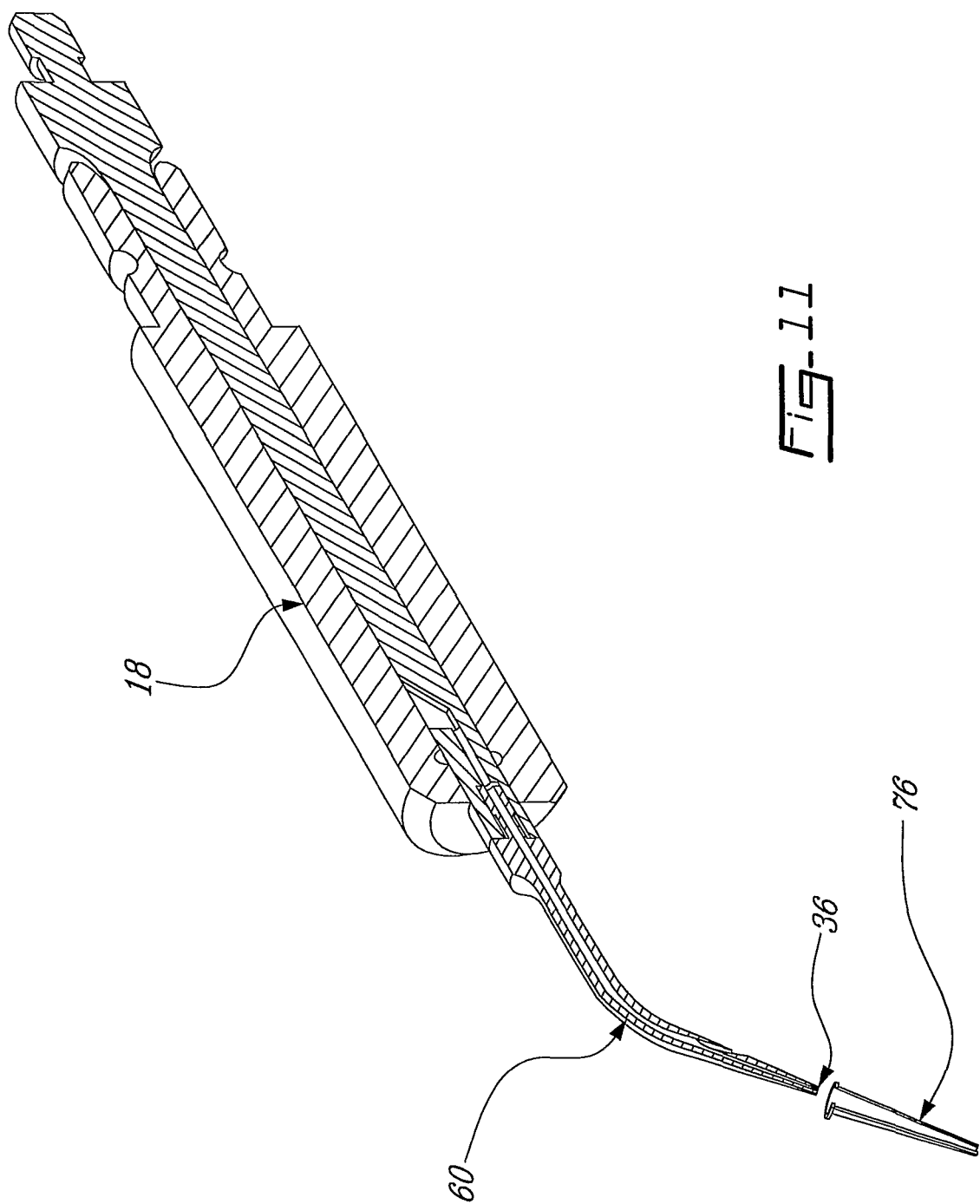

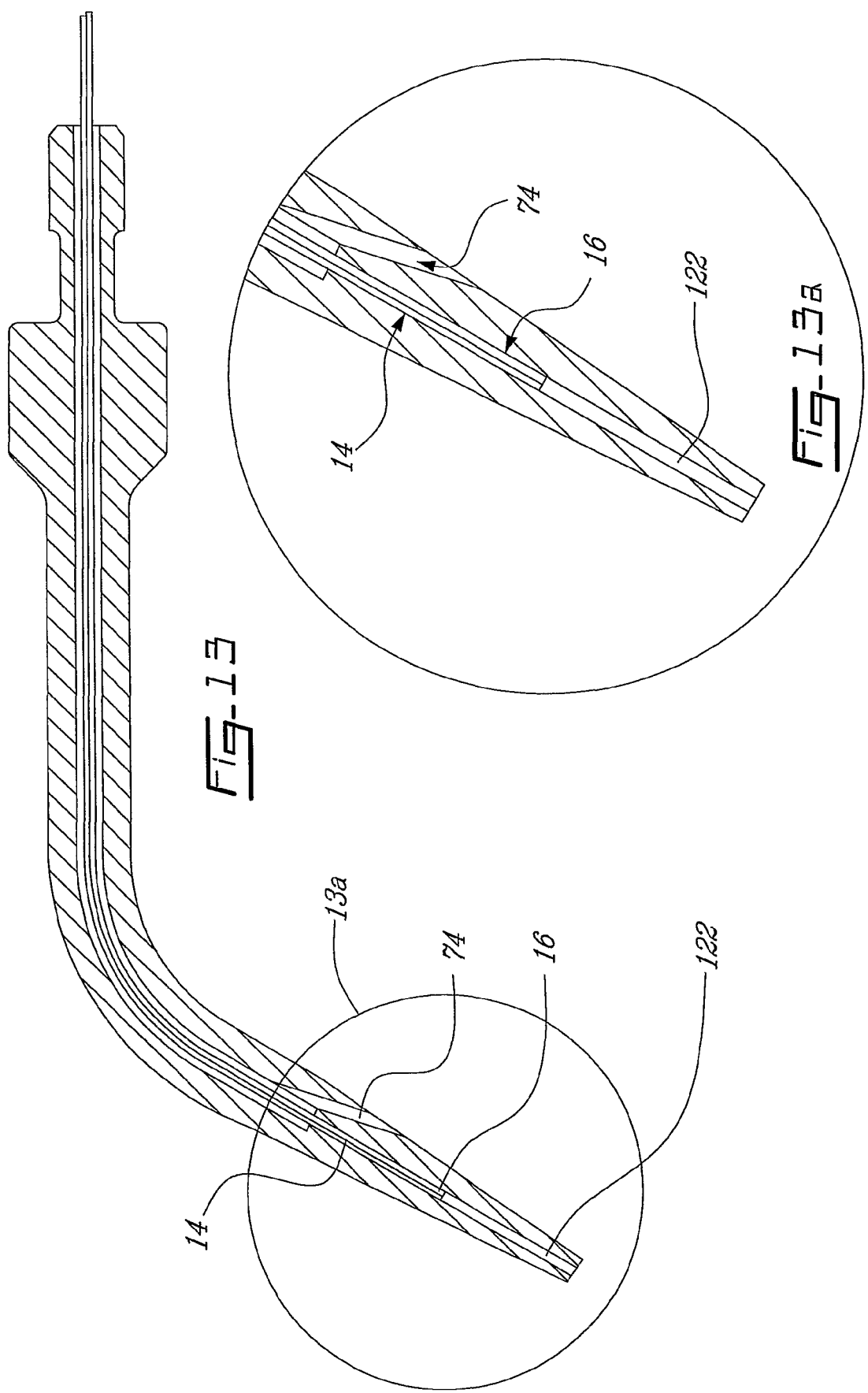

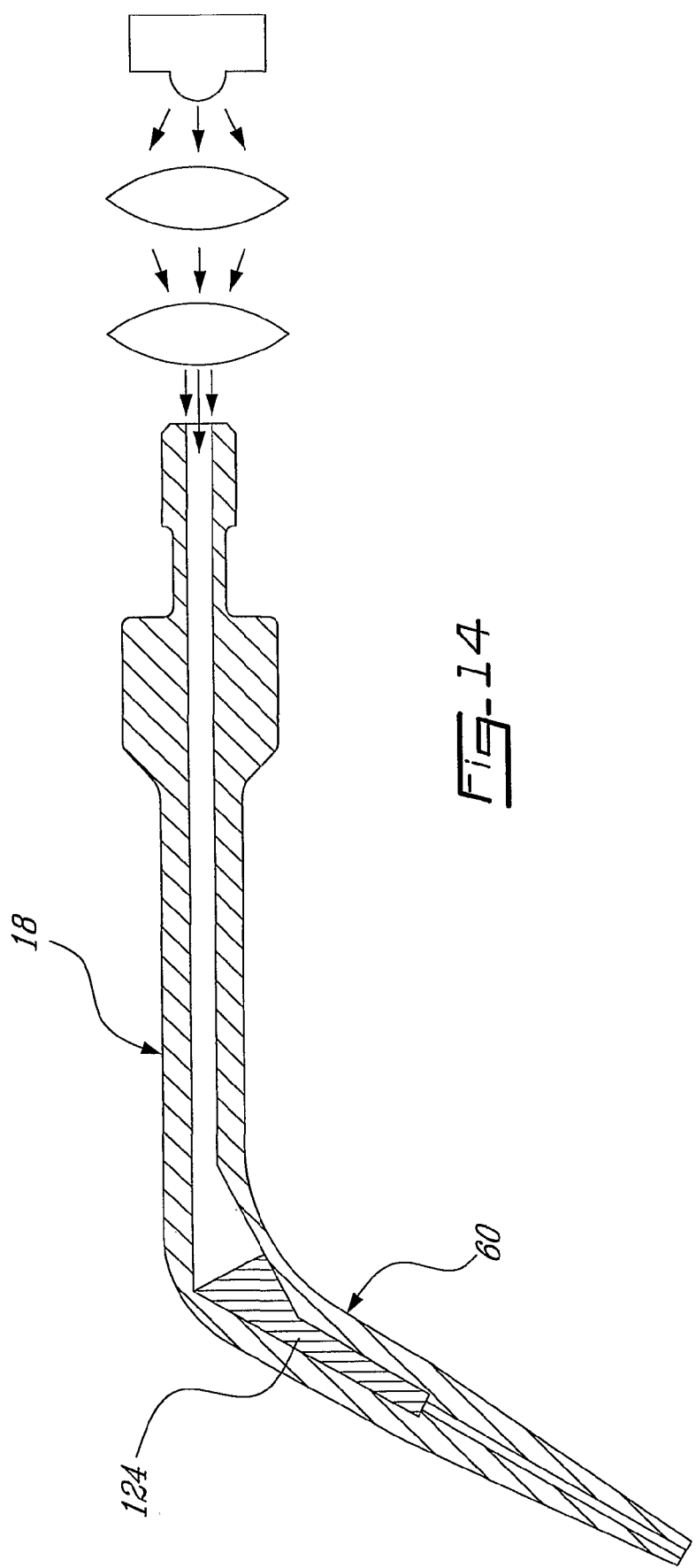

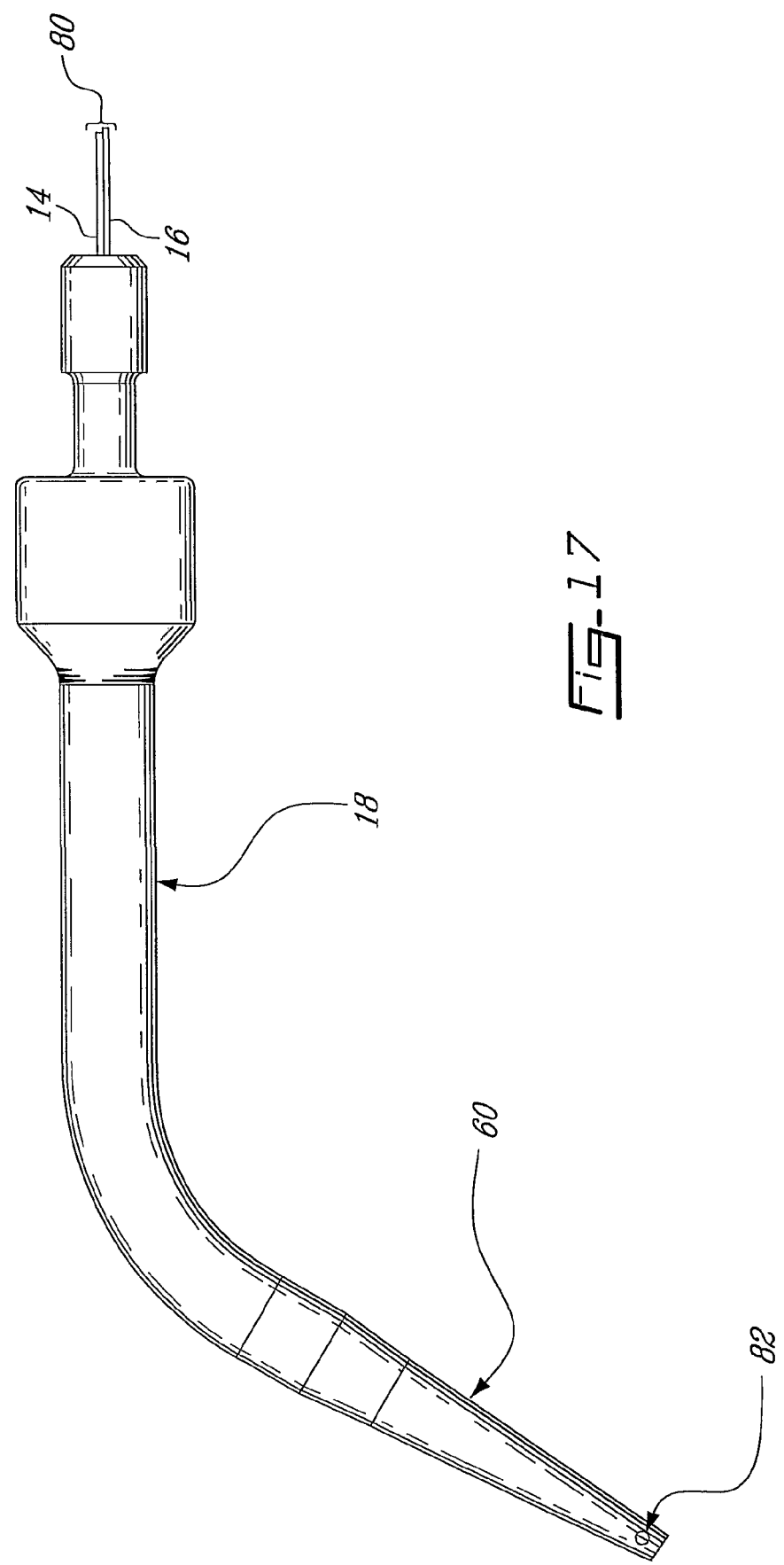

SYSTEM AND METHOD FOR DETECTION AND REMOVAL OF DENTAL TARTAR

BACKGROUND OF THE INVENTION

1. Field of the Invention

The present invention relates to the detection and removal of dental tartar and, more particularly, of subgingival tartar.

2. Description of the Prior Art

The removal of tartar, for instance with a scraper or a sonic or ultrasonic instrument, is important to prevent or to treat periodontal diseases, i.e. of tissues which surround the teeth, such as bone B, gums G, ligaments, etc. The tartar is calcified dental plaque that has accumulated on the tooth surface. Supragingival tartar and subgingival tartar S (see FIG. 2) must be removed as tartar is a porous substance which contains bacteria and which favours the accumulation of these pathogenic bacteria on its structure.

In a healthy periodontium (see FIG. 1) there is no periodontal pocket. However, when there is a periodontal disease (FIG. 2), such a periodontal pocket P is formed by an inner surface O of the gums G and by the root R of the tooth T and which is closed apically by the periodontal ligaments L. Subgingival tartar S can thus be found in this periodontal pocket P.

Therefore, to prevent periodontal problems which can lead to severe health problems, it is important to remove tartar from the tooth surface as it is forming; on the other hand, the removal of tartar is done with difficulty and in a groping manner, subgingival tartar being normally invisible to the human eye in normal conditions as it is covered by the gums. To remove subgingival tartar (i.e. located behind the gum), the operator must try to locate tartar by tactile feeling using a probe, but one cannot actually view subgingival tartar to ensure a complete removal thereof without resorting to invasive surgical procedures.

The use of an endoscopic method and device for the removal of subgingival tartar, is also known from U.S. Pat. Nos. 5,230,621 and 5,326,365. In this system, an endoscopic probe is inserted in the gingival pocket or sulcus to endoscopically visualise the process of and/or effects of subgingival root planing, scaling or other plaque removal procedures carried out by other operative instruments. Alternatively, the endoscopic viewing apparatus may be incorporated in an operative instrument which itself is used to remove deposited material from subgingival tooth surfaces, whereby the operator may view and/or guide the instrument while using the plaque removal instrument itself. Therefore, the operator looks at a monitor that provides images of the endoscopic viewing and the operator detects the presence of subgingival tartar by looking at the monitor. This system is efficient, but somewhat cumbersome to use, as the operator must stop looking into the mouth of the patient in order to look at the monitor. Moreover, this system is relatively expensive, as it requires a monitor and associated hardware.

Therefore, there is a need for a dental instrument which, using a tartar removal instrument or the like, can automatically detect the presence of subgingival tartar, which does not require the use of a monitor, and which allows the operator to concentrate on his/her task in the patients mouth by not having to look at a monitor and thus leave the patients mouth from his/her sight. Such an instrument would facilitate the operator's task of removing subgingival tartar by providing a system which assists the operator in the diagnostic while he/she is using a tartar removal instrument.

SUMMARY OF THE INVENTION

It is therefore an aim of the present invention to provide a novel system for the detection of dental tartar, including subgingival tartar.

It is also an aim of the present invention to provide a novel system for the detection of dental tartar that automatically detects the tartar based on its spectral reflectance characteristics.

It is a further aim of the present invention to provide a system in which a visual, sound-based, tactile or other, signal is given to the operator or to the tartar removal apparatus (in this last case the signal would control the instrument) following detection of subgingival tartar, wherein this detection results from measurements made in the subgingival region and taken in one or more predetermined ranges of wavelengths that are appropriate for discriminating the spectral reflectance characteristics that constitute a signature of tartar presence.

Therefore, in accordance with the present invention, there is provided a dental tartar detection and removal device, comprising a tartar removal instrument adapted to be displaced along a tooth, illumination means for illuminating with an incident light a region to be examined on, or adjacent to, the tooth, detection means for collecting the light reflected thereat, and an analysing system for providing a signal to an operator of said tartar removal instrument or to said tartar removal instrument when measurements on the reflected light in one or more predetermined ranges of wavelengths fall within any first predetermined range of values that are characteristic of tartar, or when said measurements do not fall within any second predetermined range of values that are characteristic of artefacts other than tartar, such that in response to said signal said tartar removal instrument can be operated for removing tartar at said region, or adjacent thereto.

Also in accordance with the present invention, there is provided a method for detecting and removing dental tartar from teeth, comprising the steps of: (a) providing with a detection instrument one of an incident light and a naturally present source of illumination on a region of a tooth, (b) collecting with said detection instrument and measuring reflected light from said region of the tooth; (c) analysing said reflected light to determine if said reflected light is representative of the presence of tartar; (d) providing a signal to an operator of a tartar removal apparatus or to a tartar removal instrument when presence of tartar has been detected in step (c); and (e) removing tartar from said region with said removal instrument while said detection instrument remains substantially in position in said region.

Powered tartar removal instrument or tartar removal instrument may include sonicscaler, ultrasonic scaler, rotary scaler, piezo-electronic scaler, any hand-powered instruments (e.g. curettes), or any type of instrument suited for tartar removal by a dental operator.

BRIEF DESCRIPTION OF THE DRAWINGS

Having thus generally described the nature of the invention, reference will now be made to the accompanying drawings, showing by way of illustration a preferred embodiment thereof, and in which:

FIG. 1 is an enlarged view of bubble 1-1 of FIG. 1a;

FIG. 3 is a schematic representation of a tartar removal instrument with a system for the detection of dental tartar in accordance with the present invention;

FIGS. 4 and 4a are schematic enlarged partial detailed views of the connector system of FIG. 3;

FIGS. 5a, 5b and 5c are respectively perspective, elevation and enlarged detailed views of a tartar detection and removal curette of the present invention;

FIGS. 7a and 7b are respectively longitudinal cross-sectional and enlarged detailed views of the tartar detection and removal instrument of FIGS. 4 and 4a;

FIG. 8 is a perspective view of part of a further tartar detection and removal instrument of the present invention;

FIG. 8a is a schematic view of the tartar detection and removal instrument of FIG. 8 being displaced toward, and in position against, a tooth surface;

FIGS. 9 and 9a are respectively perspective and enlarged detailed views of part of further tartar detection and removal instruments of the present invention, having disposable tips;

FIGS. 9b and 9c are respectively longitudinal cross-sectional and exploded elevation views of part of a further tartar detection and removal instrument of the present invention, having a disposable tip;

FIG. 9d is a longitudinal cross-sectional and exploded view of part of a further tartar detection and removal instrument of the present invention, having a disposable tip;

FIG. 10 is a perspective view of part of a further tartar detection and removal instrument of the present invention;

FIG. 11 is a perspective view of part of a further tartar detection and removal instrument of the present invention;

FIGS. 13 and 13a are respectively perspective and enlarged detailed views of part of a tartar detection and removal instrument of the present invention;

FIG. 14 is a perspective view of part of a further tartar detection and removal instrument of the present invention;

FIG. 17 is a perspective view of part of a further tartar detection and removal instrument of the present invention.

DESCRIPTION OF THE PREFERRED EMBODIMENTS

Figure 1:
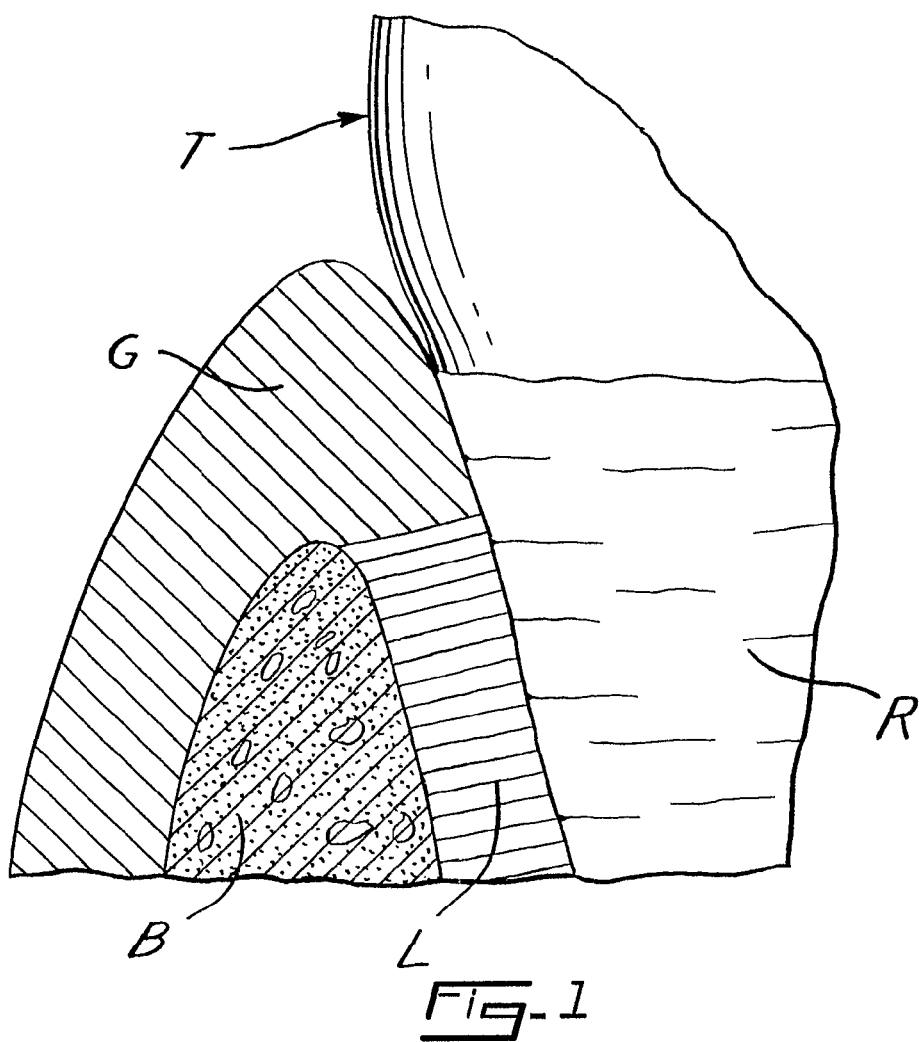
Figure 1A:
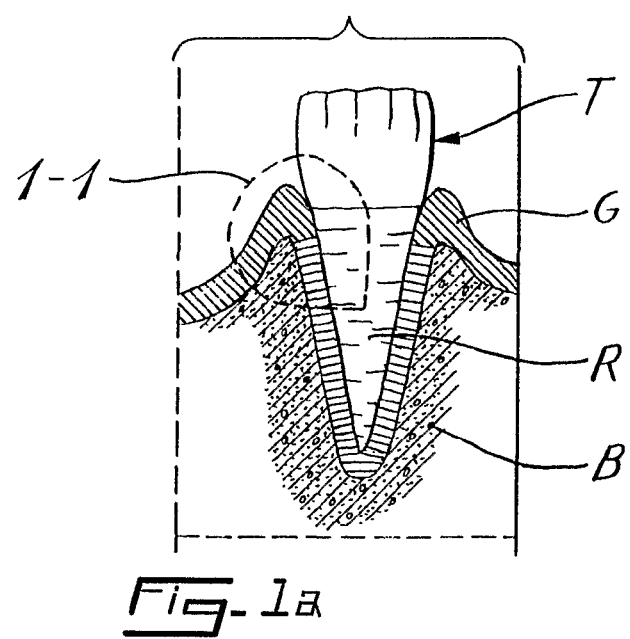
FIG. 1a is a schematic vertical cross-sectional view of a tooth and its surrounding tissues.
Figure 2:
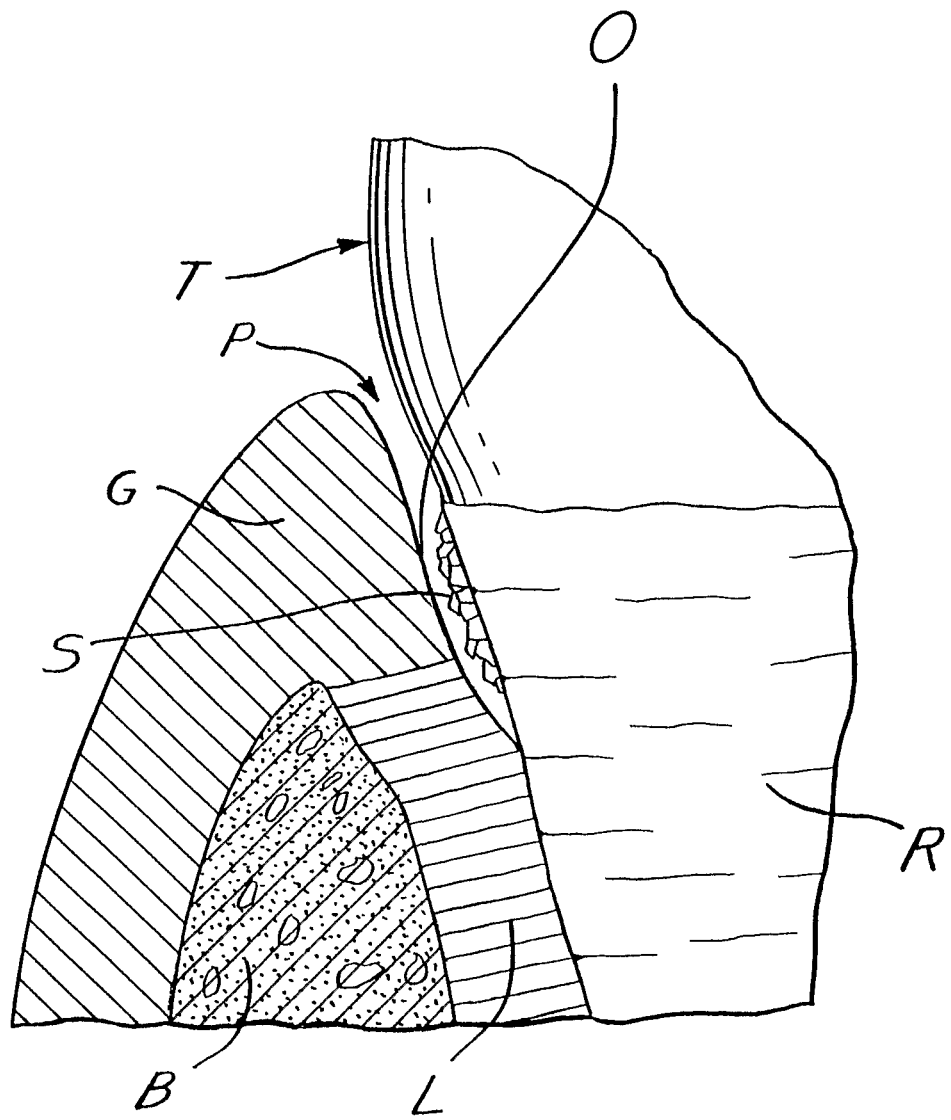
FIG. 2 is a schematic view similar to FIG. 1 but showing a periodontal pocket between the tooth's root and the gums, with subgingival tartar being shown lodged therein.

The present invention is a system 10 for the automated detection of the presence of subgingival tartar S with a tartar removal instrument adapted to act as an endoscopic-like device using an optical method based on the electromagnetic spectral reflectance properties of tartar to discriminate the tartar present on the teeth from the healthy areas thereof, from the gums, from blood, and in fact from any artefact other than tartar that such a tartar removal instrument may encounter when it is inserted between a tooth and the gums.

More particularly, the system 10 comprises three main mechanisms, that is (1) a tartar removal system including optical components, (2) a tartar detection system including a casing containing optical components, light sources, and acquisition components and signal processing electronics, as well as a water inlet (although this is an optional feature) capable of being connected to a water supply or source 30, all the components 1000 normally found in a powered tartar removal instrument (e.g. in a Cavitron® or in a curette), and including a cable strand that includes optical fibers, all the components normally found in a powered tartar removal instrument cable and which connects the tartar removal instrument insert to the casing, and (3) a control system that enables the activation of the powered tartar removal instrument of the tartar removal system upon diagnostic, with the control system being, for instance, (i) a manual control or a powered pedal activated by the operator OP, or (ii) a module (e.g. electronic components or electro-mechanic components, etc.) that activate the powered tartar removal instrument in relationship with the diagnosis.

Indeed, the system 10 comprises a powered tartar removal instrument insert 12, which herein contains at a tip thereof an optical system for detecting tartar, although such an optical system may be provided externally of this tip. The optical system herein comprises optical fibers and, more particularly, one or more illumination fibers 14 used for illuminating the subgingival region and one or more detection fibers 16 for receiving the light reflected by the examined or periodontal site for the subsequent determination of the spectral reflectance characteristics in this region (although other means than optical fibers may be used, e.g. prism, mirror, etc.). It is contemplated that a single optical fiber could be used for both illumination and detection functions. The powered tartar removal instrument insert 12 has a curved end section 60 adapted to be inserted in the periodontal pocket P with the illumination fibers 14 and detection fibers 16 being contained in this end section 60 and extending up to an open free or distal end 36 thereof and having their respective distal ends thereat. The end section 60 may be pointy, in the shape of a spatula, etc.

The powered tartar removal instrument insert 12 includes a handle 18. The powered tartar removal instrument insert 12 also includes a connector 46, which for instance is located at the proximal end of the handle 18. Water injection or feed on the subgingival region is carried out by the same system as in a powered tartar removal instrument. The periodontal pocket P is irrigated in order to provide for further detection efficiency.

The irrigation system can be used without activating the powered tartar removal instrument contrary to conventional powered tartar removal instruments where the pedal simultaneously activate the irrigation system and the powered tartar removal instrument.

Figure 6:
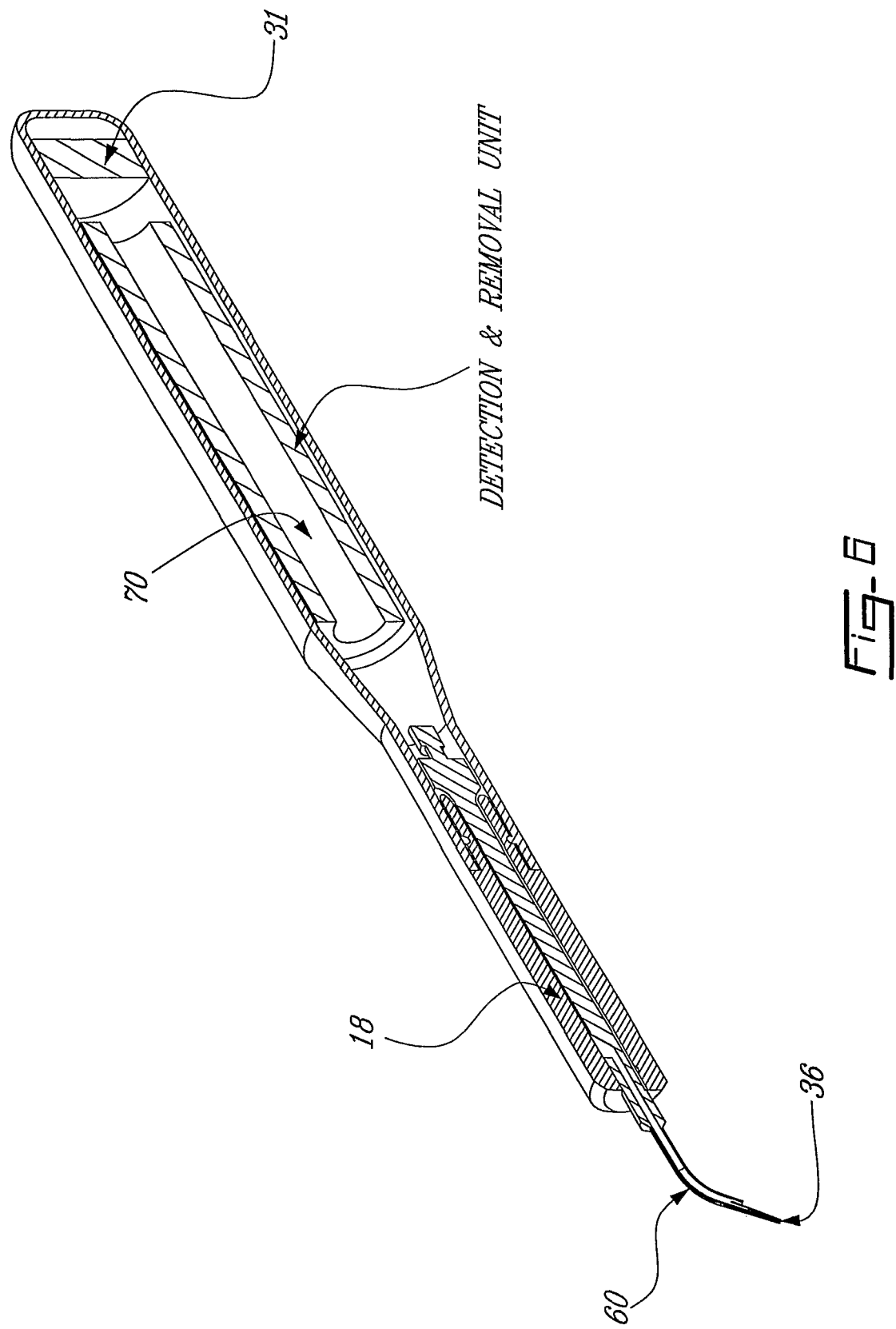
FIG. 6 is a perspective view of a further tartar detection and removal instrument of the present invention.

A cable strand 32 links the powered tartar removal instrument insert 12 to an electronic system provided in a casing 34 that could have the shape and size of a powered tartar removal instrument casing which is adapted to be connected to an outside power supply (unless the casing 34 is powered with batteries 31 placed in it, as in FIG. 6) and to the water source 30 via water supply tube 33 (that may be a portable reservoir integrated in the casing 34), thereby rendering the system S portable. The light propagated by distal sections of the illumination and detection fibers 14 and 16 in the powered tartar removal instrument insert 12 is thus further conveyed to or from the casing 34 by proximal sections of these fibers 14 and 16 that are part of the cable strand 32. The cable strand 32 carries and protects the illumination and detection fibers 14 and 16 and the components normally found in a powered tartar removal instrument cable (which includes part of the water supply tube 33 and electric power for the insert). The cable strand 32 is detachably connected to the connector 46 provided at the proximal end 33 of the handle 18 of the powered tartar removal instrument insert 12 so that the powered tartar removal instrument insert 12 can be detached from the cable strand 32 for allowing the powered tartar removal instrument insert 12 to be sent alone to a sterilisation apparatus, such as an autoclave, a chemiclave, etc. The connector 46 herein acts as a connector of optical fibers which thus permits the insert to be detached from the cable strand 32, but it is also contemplated not to have such an optical connector as long as there is a connector that allows the insert 12, or a part thereof, to be detached from the rest of the system so as to allow for the sterilisation of the relevant part of the insert. Alternatively, the powered tartar removal insert 12 could also be of the single-use type and would thus be discarded instead of sterilised.

Each of the one or more illumination fibers 14 provided to illuminate the site (i.e. the periodontal pocket P) has one of its extremities facing a light source (which may be provided or not with an optical wavelength selective filter) and its other extremity at the distal free end 36 of the powered tartar removal instrument insert 12. Each such fiber 14 is interrupted (or sectioned) at the connector 46 between the cable strand 32 and the powered tartar removal insert 12.

Each of the one or more detection fibers 16 (which may be the same one as that or those optical fibers 14 used for "illuminating" the periodontal pocket P) is used for receiving the reflected "light" (electromagnetic waves: UV, visible light, IR, etc.) coming from the periodontal site. Each such detection fiber 16 has one of its extremities at the distal end 36 of the powered tartar removal instrument insert 12 and its other extremity facing a photodetector (or an electronic light transducer) 38 (which may or not comprise an optical wavelength selective filter). Each such fiber 16 is interrupted (or sectioned) at the connector 46 between the cable strand 32 and the powered tartar removal instrument insert 12. An electronic or optical filter can be provided anywhere along the electronic or optical path.

This detector 38 is connected to an electronic system housed in the casing 34.

At the detector or from the signal delivered by the detector, there may be an electronic or physical (optical) filtration system to ease the detection, for example to remove from the received wavelengths those that result from non-tartar structures or that are not necessary for the detection and therefore enhance the significant signal. The filtration system can also divide the signal from two or more different spectral regions.

The signal obtained after this filtering or directly from the detector without any filtering is then analysed by an electronic processor to determine whether tartar is present at the distal end 36 of the powered tartar removal insert 12 or not.

If tartar is detected, an indicator (luminous, sound, or any other means sensible by the operator) is actuated so that the operator is informed of the presence of tartar in the region being examined by the distal end 36 of the powered tartar removal instrument insert 12. Simultaneously to inform the operator or without informing the operator the system could, when tartar is detected, power the tartar removal instrument insert 12 by actuating a control box 400 to enable the removal of the tartar at the distal end 36 of the powered tartar removal instrument insert 12 at that moment. For instance, the indicator can take the form of a luminous indicator 42 located on the powered tartar removal instrument insert 12 to which light generated in the casing 34 is conveyed by one or more optical fibers 44 between the casing 34 and the handle 18 of the powered tartar removal insert 12 such as to terminate at the indicator 42 provided on the handle 18 (see also FIGS. 7a and 7b), and such that the operator can see the light conveyed by the optical fibers 44 upon detection of tartar. Also, the luminous signal could come from a warning LED (light emitting diode) positioned on the handle 18 and electrically connected to a switch located in the casing 34 and triggered automatically upon detection of tartar.

The connector 46 at the end of the cable strand 32 again provides a detachable connection mechanism between the handle 18 of the powered tartar removal instrument insert 12 and the cable strand 32 (see FIGS. 4 and 4a). The cable strand 32 is again a flexible sheath for the illumination and detection optical fiber(s) 14 and 16, the components normally found in a powered tartar removal instrument cable (which includes a water supply tube and electric power) and the optical fiber(s) 44 for the luminous indicator 42 on the powered tartar removal instrument insert 12, if any.

The casing 34 may include an electrical input power supply 48 (the power supply can be internal or external); one or more light sources 50 (halogen bulb, diode, laser, laser diode) which may be or not filtered by an optical wavelength selective filter; the photodetector 38; an electronic processor (at least one transistor) and a memory chip that can have an input for an electronic card 40 (which could serve for example to store information or to transfer information to an electronic system, e.g. computer, printer, etc.), or the like; an interrupter or switch 54; a button 401 to activate the calibrating procedure of the instrument; possibly one or more control button(s) 402 for the adjustment of the detection sensitivity; possibly one or more control(s) 403 buttons for the calibration to the patient's dental and periodontal characteristics; an interrupter 404 to turn "on/off" a speaker 56; the speaker 56 with a generator and an amplifier 58 to emit sounds to warn the operator of the presence of tartar, or an electronic/electric system to automatically actuate the powered tartar removal instrument insert 12 when tartar is detected (the intensity of the power may be controlled or not to be proportional to the intensity of signal corresponding to the tartar, wherein a high tartar signal would lead to a high power to the powered tartar removal instrument.

Therefore, the system 10 can transmit light having an appropriate spectral composition via the illumination fiber(s) 14 in the periodontal pocket and can retrieve the light reflected by the tissues and artefacts composing the periodontal pocket or present in that pocket via the detection fiber(s) 16 which may, or not, be distinct from the illumination fiber(s) 14. This reflected light is then detected by a photodetector 38 present in the casing 34 such as to be analysed. Depending on how the spectral composition of the incident light is altered by the reflection thereof by the tissues and artefacts present in or composing the periodontal pocket, an electronic analysis or electro-mechanical analysis (e.g. electronics or informatic algorithm) allows to determine from the signal of the photodetector if the distal end 36 of the powered tartar removal instrument insert 12 is near, or not, tartar. Therefore, if the spectral composition of the reflected light falls within the ranges previously determined for dental tartar, the electronic analysis or electro-mechanical analysis sends a sensory signal to the operator and/or activates the powered tartar removal instrument insert 12, such as by actuating the luminous indicator 42 on the handle 18 via the optical fiber 44 which conveys light generated in the casing 34 to the indicator 42, although the signal could also be given in the form of sound, vibration, etc.

In order to be adapted to existing powered tartar removal instruments (scalers, ultrasonic, piezoelectric, manual curettes, and others) that undergo wear at their working end (i.e. the part of the tartar removal instrument insert 12 that is inserted in the pocket 12 and that removes the tartar), the integration of the present optical system inside or outside of this working end requires that the optical system be designed to adapt itself to such wear. In vibrating devices, the length of the working end is reduced as it is used. Furthermore, this working end undergoes lateral wear. On the other hand, it is also possible to produce a working end that wears off very little, or not at all. This could result by providing a wear resistant coating (e.g. diamond) or by using a very hard material (e.g. porcelain, metal, etc.), or with other methods.

If optical fibers, or any optical means 80, are used in the optical system, they can be glued or simply juxtaposed to the adjacent structures (e.g. within the lumen defined in the distal or working end 60 where water can serve as a cushion). To glue the fibers, epoxy-type glues can be used. Depending on the chosen configuration, the glue can be biocompatible, sterilisable, etc.

Furthermore, for added precision and better resistance to mechanical stresses, the optical means can be fixed by welding, with silver or other alloys, to the structures.

In order to be able to pass the optical means 80 inside or outside the working end 60, there can be used conventional machining techniques, moulds, etc. (e.g. EDM machining for producing holes of very small diameter, e.g. 3 mils).

The optical fibers can have a diameter of 25 microns, or less, and this provides flexibility in the design of the working end 60.

Figure 12:
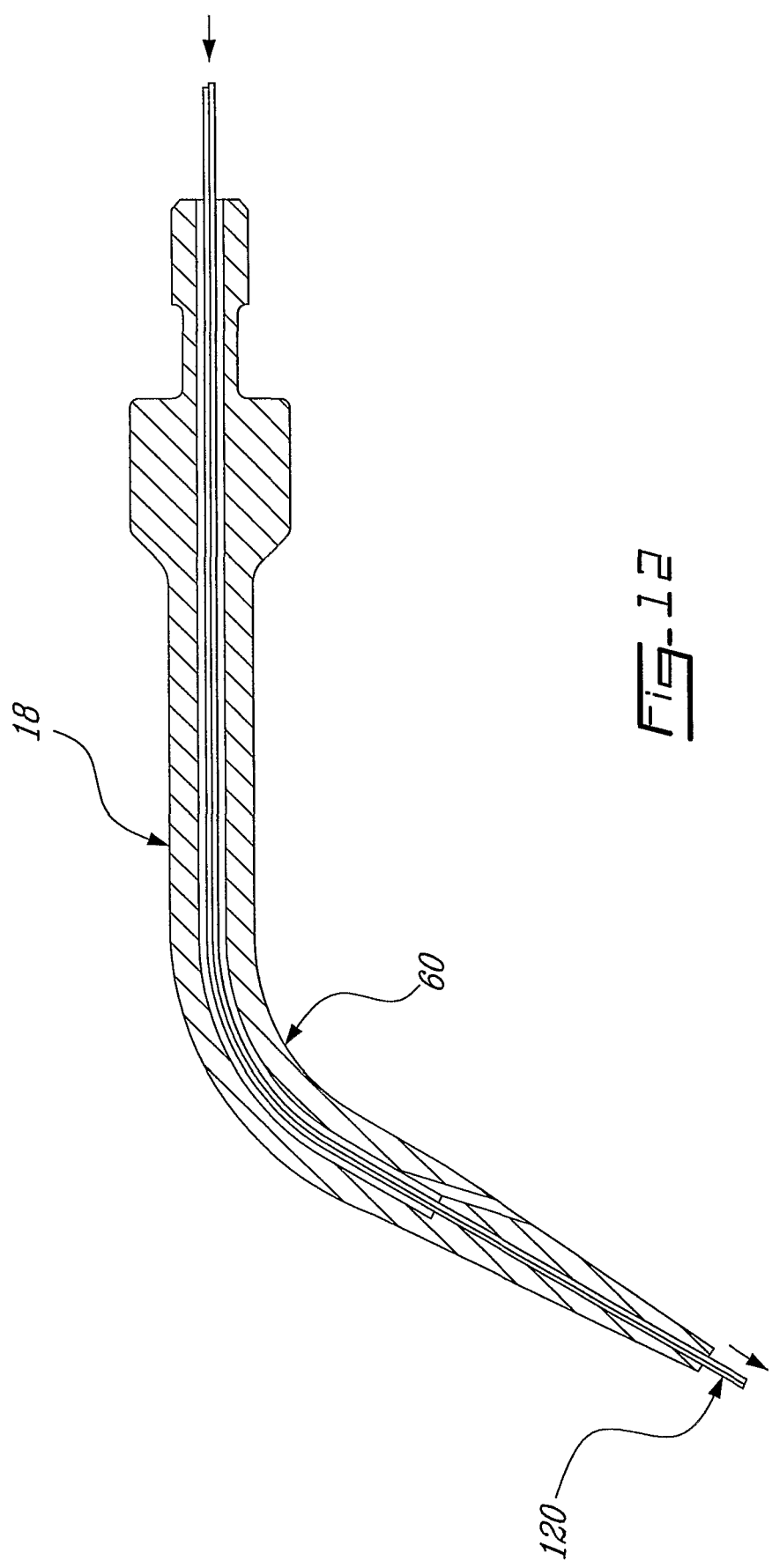
FIG. 12 is an elevation view of part of a further tartar detection and removal instrument of the present invention.

1) The optical means 80, e.g. fibers, are integrated inside the working end:
   i. Central: the optical means are positioned in the centre of the working end;
   ii. Lateral: the optical means can be inserted to have the "capturing end" 82 facing laterally instead than seeing by the bottom (see FIG. 17), and there can be a "capturing end" 82 on both sides of the curved end section 60. Because this configuration is more efficient when the tooth surface is facing the "capturing end", it is possible to have the working tip capable of rotation;
   iii. multiple optical means (illumination and collection) that are able to examine many regions at the same time;
   iv. Mobile: the optical means can move independently from the working end enabling the optical elements assembly to be displaced (see mobile optical assembly 120 in FIG. 12). Usually there is wear of the working end of a powered tartar removal instrument, having the illumination mobile is a way to adapt to that wear (see FIG. 12);
   v. Optical means at the extremity of the capturing assembly (integrated or not): an optical component, like a lens, can be used at the end of the "capturing end". This component can be used to orient the radiation in a desire manner (e.g. collecting more lateral radiation instead than from the "bottom"). For instance, an inflatable member that permits a spreading can be used. This optical component can be flexible;
   vi. Coating: a coating can be applied on the working end to prevent wear (e.g. diamond, porcelain, epoxy, plastic, etc.);
   vii. Tunnel: the part of the optical means in the working end subjected to wear can be made with a material permeable to the required radiation (see reference 122 in FIGS. 13 and 13a) and that can wear at the same rate as the working tip. For example, optical fibers can carry illumination in the working end but in the last 3 mm;
   viii. Multi optical fibres: a plurality of optical fibers can be used as optical means;
   ix. Mono: a single fiber can be used as the optical element for both illumination and collection;
   x. Other optical components: the optical means can be made with mirrors and/or prisms (see reference 124 in FIG. 14), or other diffractive or reflective optical components. The insert could also be designed so as to spread the gum such that viewing is enhanced.

2) The optical means 80, e.g. fibers, are external to the working end 60 (see FIGS. 8 and 8a): the optical means can be placed in an independent assembly externally of the working end structure. Having this part of the optical component externally enables to keep it unaffected by the eventual wear of the working end structure. For example, this external system can be composed of a tube 84 having a very small inside diameter that contains the optical means. This assembly is inserted in parallel to the working end 60. This optical assembly can be displaced by the working end (see FIG. 8) to view the tooth surface TS (see FIG. 8a). This type of assembly also provides more flexibility in the positioning of the capturing end 60. This system can also be designed to adapt to any powered removal instrument, and can thus be universal. This system can be disposable. The optical means can, as above, be multiple, have a coating, be of the tunnel configuration, be of the multi optical fibres configuration, be of the mono fibre configuration, or use other optical components.

3. Replaceable parts (integrated configuration)
   i. Replaceable parts alone or in combination:
      1. Extremity: the extremity of the working end can be the replaceable part, with or without the optical means;
      2. Working end: the working end itself can be the disposable part, with or without the optical means. For instance, both the working end and the optical means may be disposable (see FIGS. 9b and 9c), or the working end may be disposable while the optical means is permanent (see FIG. 9d) with the working end having the form of a sleeve defining a lumen in which the optical means is slidably inserted;
      3. Optical fiber assembly (e.g. mobile optical fibers): the optical fiber assembly can be disposable, e.g. a monofiber optic in plastic, glass or any other material; e.g. an optical cable can be fed through the lumen of the working end, or externally thereof, like some soft or hard tissues lasers instruments that use continuous fiber optic optical feeding systems;
      4. Covering or coating: the working tip can be covered by a covering 76 (see FIG. 11) to protect it against wear. Such a covering can be used when the optical means is integrated, as well as when it is external. The covering can be made of metal or Teflon; it can be flexible (e.g. Mylar, ptfe), curable. The covering can define a hole to allow radiation to sufficiently pass at the level of the capturing end of the optical means. It May not have such a hole (or holes) as long as it is made of material that sufficiently allows the electromagnetic waves to pass.
   ii. Fixation method
      1. Screw—pressure: a screw that pushes on the working end can secure it;
      2. Friction, radial tightening—common chuck or burr fixation system;
      3. Press-fit;
      4. Adhesive—using an adhesive that, for instance, disintegrates in the autoclave to allow for the removal of the replaceable part; it can be curable with radiation (blue, UV, etc.);
      5. Screwed by rotation e.g. air sonic apparatus: a screw thread is provided on the working end or on the replaceable part thereof, thereby allowing it to be fixed to the other portion of the working end or to the vibrating portion in the handle of the insert.

4. Materials that can be used in the construction of the working end and that are preferably resistant to wear:
   i. Titanium;
   ii. Stainless steel, series 400, e.g. 420; hardened, hammer-hardened, cold-drawn or cold-rolled metal;
   iii. other stainless steels;
   iv. Ceramic;
   v. Plastics;
   vi. other suitable metals;
   vii. other suitable materials.
5. Optical elements, including:
   i. Glass fibers;
   ii. Fibers made of other materials;
   iii. Plastic fiber (polyester, etc.);
   iv. Transparent glue;
   v. Multi;
   vi. Mono;
   vii. Bi;
   viii. Prism: a prism that causes the light to deviate in the right direction constitutes a way to canalise the light in the desired direction. Such an optical means can be used exclusively in the case of a wireless-handpiece where the radiation is directly focussed on the prism that deviate the light in the desired direction;
   ix. Mirror;
   x. Transparent porcelain (ceramic).

FIGS. 9 and 9a show two different disposable tips 90 and 92 that are detachably secured to the handle 18, or other, respectively by way of a fastener 94 (e.g. clamp, nut, etc.) or of any of a threaded engagement, a clip, a bond, brazing, etc. (see connection at reference 96 in FIG. 9a). FIG. 10 shows a further disposable tip 98 that is detachably secured to the handle 18, or other, via a clamp 99.

FIGS. 9b and 9c show a further disposable tip 132 that is detachably secured to the handle 18, wherein both the working end and the optical means are disposable, and wherein there is an optical connection 133 between the permanent section of the optical means 80 and the disposable section thereof located in the disposable tip 132.

In FIG. 9d, there is shown a further disposable tip 134, wherein the working end is disposable while the optical means 80 is permanent, with the working end having the form of a sleeve defining a lumen 136 in which the optical means 80 is slidably inserted.

All of the disposable tips herein described may not be disposable per se, as they can simply be removable for their sterilisation before being returned to curved end section 60 so as to be re-used.

FIGS. 5a to 5c show a modified manual curette 130 that is provided, in accordance with the present invention, with optical means 80 extending up to its curved end section 60 and terminating at a capturing end 82, such that the curette 130 can detect the presence of tartar and then be used, as per its conventional removal function, to remove the tartar so detected.

Figure 4B:
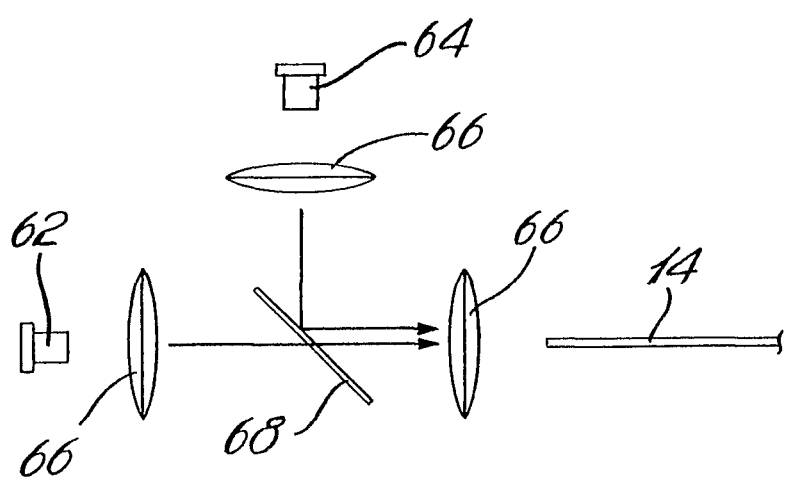
FIG. 4b is a schematic detailed view of some components of the casing of FIG. 3.

With reference particularly to FIG. 4b, the illumination fiber(s) 14 is (are) used to carry light from two LEDs 62 and 64, having different emission spectra and located in the casing 34, up to the distal end 36 of the powered tartar removal insert 12. The light emitted by the two LEDs 62 and 64 is coupled into the illumination fiber(s) 14 and, for this coupling, a dichroic mirror is used, also called a dichroic beamsplitter, as it is selective in wavelengths in transmitting light to pass within a range of wavelengths while reflecting light in another range of wavelengths. Such a dichroic mirror or dichroic beamsplitter is also called hot mirror or cold mirror, depending on the wavelength ranges for which the mirror is reflective or transmissive. A set of lenses in a "Y" configuration, or any suitable means, may also be used instead of the dichroic mirror or dichroic beamsplitter to combine the light beams emitted by the LEDs 62 and 64 and couple them into the illumination fiber(s) 14. In FIG. 4b, which illustrates the coupling in the illumination fiber 14, numeral 66 refers to lenses while numeral 68 is for the dichroic beamsplitter which is at around 45 degrees, or any other suitable angle, and which transmits the light in the wavelength range emitted by LED 62 and reflects the light in the 5 wavelength range emitted by LED 64

The LEDs 62 and 64 are chosen based on the spectral bands in which the reflectance properties of tartar are different from the reflectance properties of the other artefacts which could possibly be encountered by a powered tartar removal instrument insert inserted between a tooth and its gum (healthy or non-healthy parts of the tooth and gum), and this even when blood is present. In fact, in these spectral bands, the spectral transmission of blood has minimal effect. The choice of the spectral bands was determined by a spectral study of the reflectance properties of tartar for the wavelength range of the electromagnetic spectrum between 400 nm and 1,000 nm. This spectral study was conducted in the presence and in the absence of blood. LED 62 emits in the red area of the spectrum and its emission spectrum has its peak at approximately 625 nm and extends from 600 nm to 650 nm. For LED 64, its emission spectrum extends between 800 nm and 920 nm. The LEDs 62 and 64, or any other appropriate light source, could also operate with other wavelengths that are appropriate for the discrimination of tartar, such as in the green region of the spectrum.

With respect to the detection principle used in the present system 10, it operates on the basis of the following. The light reflected by the artefacts that composes or are present in the periodontal pocket P is received by the detection fiber 16 and is conveyed to a photodiode located in the casing 34 so as to be transduced into an electric signal. The electronic detection of the light reflected by the tooth and transmitted by the detection fiber(s) 16 operates under the "lock-in" detection principle (also referred to as phase-sensitive detection), although other signal processing approaches could be contemplated. Generally, this principle consists in modulating the intensity of a light source at a given and known modulation frequency (which should not be confused with the optical frequency of the light source). The modulated light is sent onto the medium being inspected and the light, resulting from the interaction with the medium, is detected with a photodetector that converts it into an electric signal. This electric signal is then demodulated such as to extract therefrom only its component having the frequency at which the light source was modulated. This principle allows for the detection of very small signals with great efficiency In the system 10, there are two light sources (i.e. the LEDs 62 and 64, although there could be more or less, e.g. 1 or 3 LEDs) that are modulated at different frequencies, thereby permitting the detection of the light emitted by both LEDs with a single photodiode by demodulating the electric signal of the photodiode at the two modulation frequencies of the LEDs to obtain a measurement of the amount of the light reflected by the tooth in the two spectral bands associated with the LEDs 62 and 64. These levels appear as signals V1 and V2 at the outputs of the two lock-in circuits associated with the emission channels of the LEDs 62 and 64, respectively, and are used by the electronic analysis or electromechanical analysis (e.g. processing algorithm).

The lock-in detection is herein used for two purposes:

(1) it allows to electronically separate (at the detection) the light of both chosen spectral bands impinging on a single detector, and (2) the light levels reflected by the tooth and then detected are very weak and the lock-in method is exploited for its sensitivity. The signals V1 and V2 at the exits of the lock-in circuits are processed in real time by an electronic processor integrated with the rest of the electronic components of the casing 34. The processing algorithm (or other) is programmed in this processor. The processing algorithm (or other) produces the ratio of these two signals V1 and V2, y=V1/V2 (the order in which this ratio is taken is irrelevant). If this ratio is in a range of values associated with tartar (this range having been previously established using calibration measurements), then the powered tartar removal insert is located on tartar. In this case, the algorithm (or other) sends a signal to activate a warning sound (that can be deactivated by the operator, if desired) and to activate the warning LED in the casing 34 with the light of the warning LED being transmitted through the optical fiber(s) 44 and being visible through the indicator 42 located on the powered tartar removal instrument insert handle 18.

To determine the range of values of the ratio y associated with tartar, a large number of measurements are taken on teeth at various healthy locations thereof and where there is tartar, and this with different levels of blood. By knowing, for each of these measurements, if it was taken on a healthy part or where there is tartar, data are obtained for each of these two situations. By bringing the histograms of these data on a graphic, the range of values associated with tartar is determined. The results obtained with this detection method are much more effective than those obtained with conventional tactile detection.

The operator (1) uses the powered tartar removal instrument insert to determine where there is tartar and then (2) proceeds to removing the tartar in a conventional manner by powering the powered tartar removal instrument insert 12 in regions where tartar has been so detected. The operator then (3) verifies with the powered tartar removal instrument insert that the removal of subgingival tartar is complete, and steps (2) and (3) are then repeated until no tartar is detected. The operator can also control the supply of water (see water inlet 72 and outlet 74 in FIGS. 7b, 8, 9, 13a and 13b) to the periodontal pocket P by adjusting the position of the water regulator 28. The solenoid valve 105 may be operated via a foot pedal 106 to enable water supply, or with a control provided on the handle 18 of the powered tartar removal instrument insert 12. When the operator OP receives a sensory stimulation or signal (e.g. from the illumination of the optical fiber 44, through the indicator 42, or any other means of indication in replacement or in addition to the indicator 42, such as a buzzer, vibrations, etc.) from the electronic system, the operator knows that there is some subgingival tartar at the location of the distal end 36 of the powered tartar removal instrument insert 12 and thus visually notes the position of the distal end 36 of the powered tartar removal instrument insert 12 such that the operator can then proceed with step (2) which again consists in using the "powered" powered tartar removal instrument insert for removing the remaining tartar at that location.

The powered tartar removal instrument insert 12 may be used only as a tartar detection mean.

The powered tartar removal instrument insert 12 may be used only as a tartar removal instrument.

The powered tartar removal instrument insert 12 could be powered ON continuously and used more specifically in regions where tartar is detected.

The operator may use his tactile judgement or other information to determine if he/she is in agreement with the system 10, and intervene if desired (e.g. intervene by interrupting the automatic actuation of the powered tartar removal instrument depending on the diagnosis).

Here, for coupling the light from the LEDs 62 and 64, a particular approach has been presented using a dichroic mirror and lenses, but any other configuration, such as a "Y" configuration, which allows to couple the light from the LEDs into the fibers would do as well, the fundamental point being the coupling of light into the fibers 16.

Figure 15A:
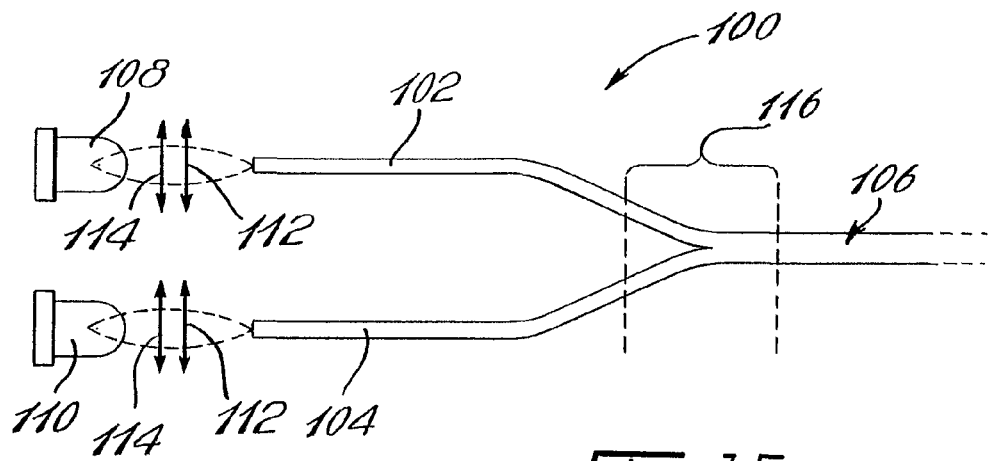
FIGS. 15a, 15b and 15c are schematic views of three methods for combining a number of light beams and coupling them into one or more optical fibres.
Figure 15B:
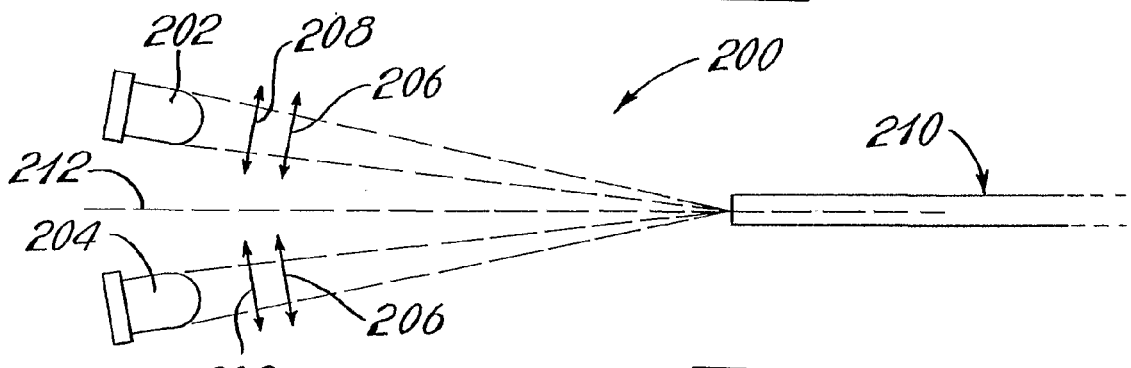

For instance, FIG. 15a illustrates a coupling 100 by fusion of two optical fibers 102 and 104 into a single fiber 106. Two LEDs 108 and 110 are used, each emitting light through a pair of lenses 112 and 114. Reference numeral 116 denotes a fused region. This method is commercially known as a WDM coupler FIG. 15b illustrates another coupling 200 which uses a "Y" configuration to couple the two lights. More particularly, two LEDs 202 and 204 are positioned each behind a pair of lenses 206 and 208 such as to emit light therethrough. The lenses 206 and 208 focalise the light on the extremity of an optical fiber 210. Reference numeral 212 denotes the optical axis of the fiber 210.

Figure 15C:
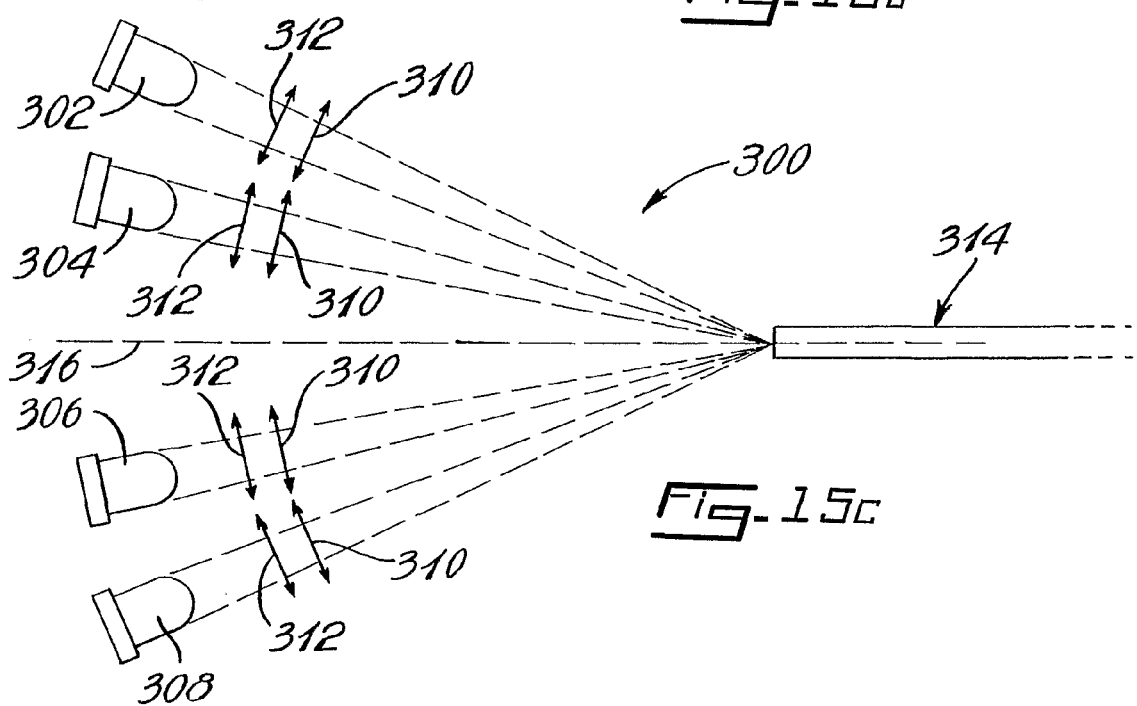

FIG. 15c illustrates a further coupling 300 which also uses a "Y" configuration but here to couple four lights that are produced by four LEDs 302, 304, 306 and 308 positioned each behind a pair of lenses 310 and 312 such as to emit light therethrough. The lenses 310 and 312 focalise the light on the extremity of an optical fiber 314. Reference numeral 316 denotes the optical axis of the fiber 314. It is noted that in a further coupling, also in a "Y" configuration, there could be three LEDs instead of the two and four LEDs found respectively in just-described couplings 200 and 300 of FIGS. 15b and 15c.

Also, as regards the detection principle described above (i.e. the lock-in detection), other principles could be used as well. Any approach that can deliver signals that are sufficiently insensitive to noise to provide for discrimination between tartar and other artefacts that can be found in a periodontal pocket P can be considered. Furthermore, in a numeric system, there could be used for instance two LEDs having different wavelengths (but possibly of same frequency) e.g. a red and a green LED, which are activated repeatedly one after the other and with a delay there between.

As an alternative to the processing algorithm presented hereinabove (or other), combinations of the signals V1 and V2 other than the above ratio y could be considered. Indeed, the classification of the data into "is tartar" and "is not tartar" could be done in a two-dimensional space, for instance by plotting V1 versus V2, or any other function of V1 and V2 versus another function of V1 and V2 that is independent from the previous function. Also, if more than two LEDs or other sources of light (such as lasers, halogen lamps, spectral lamps, filtered lamps, etc.) are used, information can be gathered and analysed in two or more dimensions Furthermore as an alternative to the approach just described, a spectrometer could be used to measure a spectrum of the light reflected by the tooth and this spectrum would then be analysed with an algorithm (or other) to determine if it corresponds to a spectrum of tartar or to a spectrum of another artefact. Any other suitable method may be used to analyse the spectrum received and compare it with the spectrum of tartar with a view to detecting the presence of tartar.

The present system could, by varying the spectrum to be detected, be used to locate other structures having distinctive spectral characteristics and positioned in a buccal site where access is limited (e.g. dental decay, periodontal ligament, inflamed gum [high content in blood], dental plaque, dental fillings, melanoma, any marked substance with a tracing substance, etc.). For instance, dental plaque could be detected by entering in the detection system the parameters that correspond to the plaque limits. Furthermore, on the basis that a colorant like erythrosyne is adapted to reveal the presence of plaque (it is used as an educational tool with patients), entering the spectral parameters of such a colorant could provide an alternate way to detect plaque. As periodontal treatments may more and more become oriented towards the selective removal of tartar and plaque as opposed to the aggressive treatment of the dental surface to render this surface smooth, a plaque detection system would permit to remove plaque with limited force and tartar with more force, and thus preserve the radicular surface (which is presently being abused by excessive scratching).

The system 10 could also include a recalibration function. A warning signal can also be provided to indicate when too much blood is present in the area being examined by the powered tartar removal insert and that the system 10 cannot make an adequate reading and thus cannot determine with sufficient precision if tartar is present on the tooth in this area.

A further feature could be included to indicate if the powered tartar removal instrument insert or, more specifically, the illumination and/or detection fibers 14 and 16 thereof are too worn out to be efficiently used and should thus be replaced. Such a state could be detected by insufficient light being received in the electronic system provided in the casing 34.

In addition to providing to the operator the luminous (or other) signal that indicates the presence of tartar with an indicator (such as the illustrated optical fiber 44), the system 10 may also include a monitor that displays further information to the operator such as electronic signals within the system which would help his/her diagnostic.

There may also be included a means of 35 of collecting data from the electronic system (e.g. via a computer and software, including an electronic card 40, etc.), to be saved in any kind of storing medium for allowing the patient's history to be followed. For the present embodiment of the system 10, the reflectance properties of tartar in the range between 400 nm and 1,000 nm have been studied, and light sources in that range are used (the two LEDs 62 and 64). However, use of light sources emitting below 400 nm in the ultraviolet (UV) range or above 1,000 nm in the far infrared could also be envisaged.

Also, as the spectral responses of various artefacts other than tartar are known, such as those of enamel, of the tooth's root surface, of the gum, of blood, of tooth decay (caries), of tooth fillings, etc., it is possible to adapt, e.g. program, the system 10 so that a tartar-presence signal is given to the operator as a result of the detection of spectral characteristics that are not representative of those of the aforementioned artefacts. Therefore, if the system 10 detects only spectral characteristics of these artefacts (wherein the term "artefacts" herein excludes tartar) there is no tartar in the region under examination.

As tartar does not respond to UV light as much as other artefacts present in the periodontal pocket P, if UV light is directed onto the tooth, absence (or near absence) of fluorescence may be an indication of the presence of tartar.

Also, a tracing substance (e.g. organic dye [erythrosine]) could be used, which would adhere to tartar but not to other artefacts. By then illuminating the tooth with a light source, the tracing substance would emit at a specific wavelength such that if this wavelength is detected, tartar is present. It is also possible to use a substance which reacts with the components of tartar such that a spontaneous emission of light at a specific wavelength is emitted. This spontaneous emission of light is collected with the optical probe. If the specific wavelength is detected, there is tartar. This method may possibly be used without a light source at the patient's mouth.

It is also possible for the tartar to be detected using non-luminous electromagnetic wavelengths or by other similar methods, e.g. far infrared, ultraviolet, piezoelectric, ultrasound, magnetic resonance, shadows, etc.

An other use of the present invention would be the detection of a periodontal or a dental artefacts that has a specific affinity with a known tracing substance (e.g. reddish reflectance of erytomysine marker with dental plaque) that has a particular reflectance signature could be used to detect a desired substance that has a distinct affinity to that substance.

Means other than optical fibers (e.g. prism, mirror, transparent tubing, etc.) may be used to illuminate the teeth and to collect light reflected therefrom as long as the reflected light is of sufficient intensity to allow it to be analysed.

As previously mentioned, water is not essential to detection in the present system, although it can sometimes increase the efficiency of the detection process. The water system used in the present invention is preferably the same as that used in the configuration of the selected powered tartar removal instrument. In cases where the powered tartar removal instrument does not include a water supply, water can be supplied near the capturing end. This water supply can be delivered by an external tube, by a tube that is integrated in the working end, or by other suitable means.

It is also possible to use a compact system (see FIG. 6), wherein all, or at least most, of the detection system is located in the handle, including a water tank 70. This configuration allows to reduce the necessity of having optical fibers in the cable strand, or even not to have any optical fibers, in which case the luminous signal emanating from the illumination system is used directly and is deviated via optical components towards the extremity of the working end (see FIGS. 14a and 14b). This compact system may contain all of the required components. Water delivery may be internal or external.

The present invention could also include periodontal pocket measuring device(s) that would enable the measure of the depth of a periodontal pocket and those measurements could be transmitted electronically to a computer or the like.

The automated detection system could be replaced by a display screen or an equivalent mode to transfer an image of the region under study while the operator is performing the scaling.

Even though the present invention proposes a detection system having high sensitivity and specificity, it is possible to combine one or more detection systems to obtain even better or more reliable results (e.g. with systems relying on the analysis of responses in different regions of the electromagnetic spectrum or of responses resulting from illumination with different intensities of an electromagnetic spectral region).

It is possible to use an illumination system that illuminates independently of the collection system by illuminating the tooth and its periodontal site (e.g. via the tooth's occlusal), while using an independent collecting system to collect radiation from the illuminated site.

There are three diagnostic methods that may be used in the present invention. First, a mean is used to transfer the visual information incoming from the collecting means to the operator such that the operator can make the diagnosis based on the image displayed. Second, a mean is used to convert the radiation collected into a stimulus to the operator such that the operator can make the detection of tartar (e.g. converting a collected IR radiation into a visible radiation corresponding to the first radiation collected or converting this first radiation into an audible stimuli corresponding to this first radiation). Third, the system herein presented more explicitly is used, wherein the electronic-electric treatment of the collected radiation determines if the radiation corresponds to tartar.

The minimum requirement for the present detection system to be functional is the characteristic of the collected radiation. The system basically collects the intensity of the radiation that has resulted from the illumination of the site being observed. Therefore, it is possible to detect tartar by comparing the total intensity of the collected radiation CR to a predetermined value (or range of values) corresponding to tartar. Other secondary parameters may also be monitored.

It is noted that the collection of radiation from the observed site can be done directly or indirectly. The radiation issuing from the observed site can pass through blood, water, plaque, other substances introduced in the periodontal pocket (fluorescent liquid, etc.), or other, before being collected by the collected system.

The radiation can also be modified at the tip of the capturing end of the optical means by one or more optical elements (e.g. flexible lens) that modify the behaviour of the electromagnetic radiation depending on its optical or mechanical interaction with tartar or with other non-tartar substances.

Figure 16A:
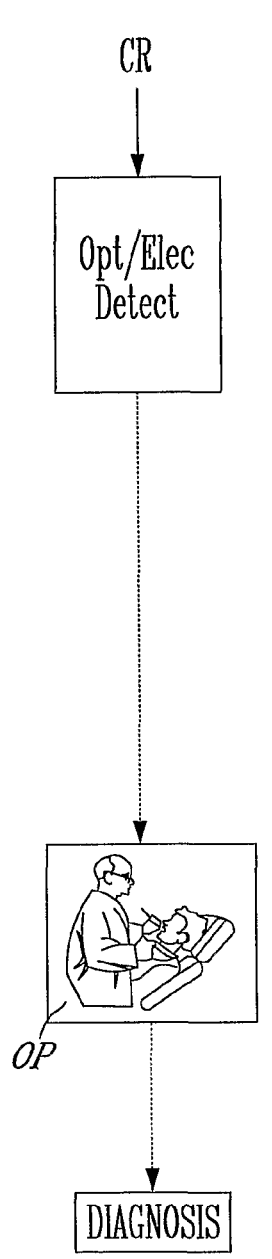
FIGS. 16a, 16b and 16c are schematic views illustrating three diagnostic sequences.
Figure 16B:
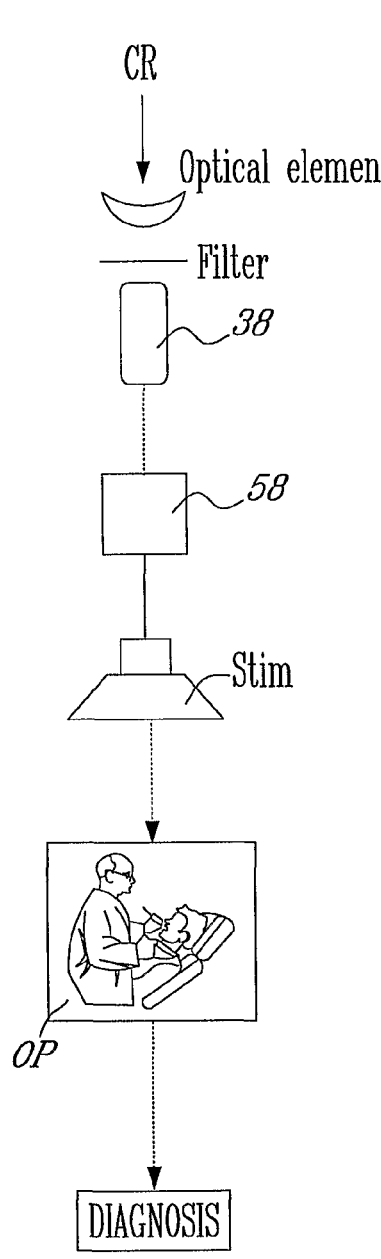
Figure 16C:
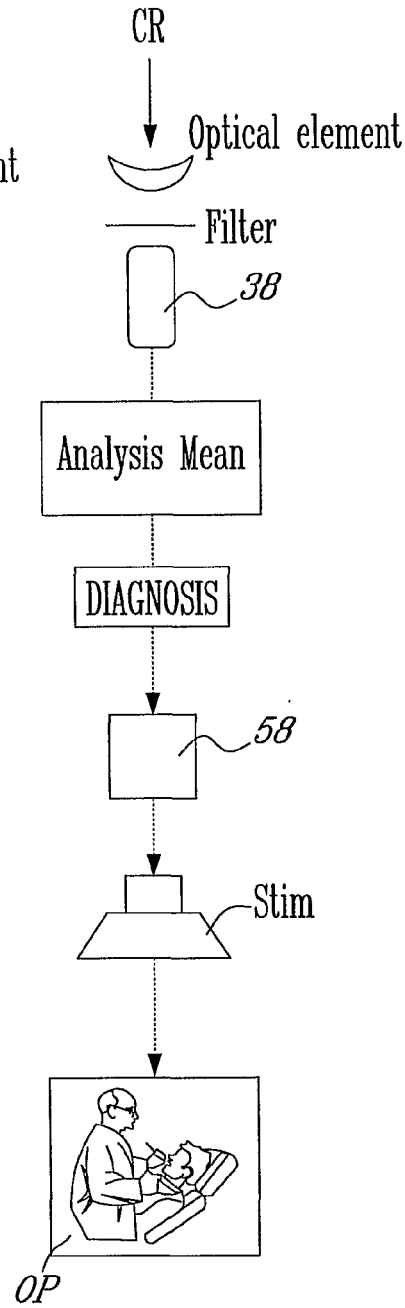

FIGS. 16a to 16c illustrate three diagnostic sequences as follows. FIG. 16a shows a diagnostic sequence using an optical collection and a display device, wherein the diagnostic is done by the operator, for instance by using a magnifying lens positioned in front of the optical fiber so as to display the color of the collected signal. In FIG. 16b, there is illustrated a diagnostic sequence using an optical collection, electronic transformation and a display device, wherein the diagnostic is done by the operator, for instance by converting an infra red ray, which is invisible to the eye, into a luminous ray. FIG. 16c shows a diagnostic sequence using an optical collection, wherein the diagnostic is done by a system in accordance with the present invention, and is communicated to the operator and/or to the machine.

The invention claimed is:

1. A dental tartar detection and removal device, comprising a tartar removal instrument configured to be displaced along a tooth,
    a light source that emits incident light at two or more wavelengths, including at least one wavelength in the infrared range which transmits through one of blood and water, to illuminate a region of the tooth, to be examined, or adjacent to the tooth,
    a spectral reflectance detector for collecting light reflected thereat, and
    an analysing system for providing a signal to an operator of said tartar removal instrument or to said tartar removal instrument when measurements on the amount of reflected light in one or more predetermined ranges of wavelengths fall within any first predetermined range of values that are characteristic of tartar, or when said measurements do not fall within any second predetermined range of values that are characteristic of artefacts other than tartar, such that in response to said signal said tartar removal instrument can be operated for removing tartar at said region, or adjacent thereto.

2. A device as defined in claim 1, wherein said light source and said spectral reflectance detector are provided adjacent said tartar removal instrument such that said light source and said spectral reflectance detector remain at a site being examined while said tartar removing instrument is operated to remove detected tartar.

3. A device as defined in claim 2, wherein said first predetermined range of values cover wavelengths associated with spectral reflectance characteristics of tartar.

4. A device as defined in claim 1, wherein said tartar removal instrument comprises a distal end with said light source and said spectral reflectance detector terminating substantially adjacent said distal end.

5. A device as defined in claim 4, wherein said light source and said spectral reflectance detector extend within said distal end of said tartar removal instrument.

6. A device as defined in claim 4, wherein said light source and said spectral reflectance detector extend externally along said distal end of said tartar removal instrument.

7. A device as defined in claim 4, wherein distal ends of said light source and said spectral reflectance detector are directed laterally of said distal end of said tartar removal instrument.

8. A device as defined in claim 4, wherein said light source and said spectral reflectance detector comprise at least one optical fibre having a distal end located adjacent said distal end of said tartar removal instrument, such that said incident light emitted by said light source is transmitted by said optical fibre to said distal end thereof and to the tooth.

9. A device as defined in claim 8, wherein said light source and said spectral reflectance detector each comprises one said optical fibre, said distal end of each said optical fibre being located adjacent said distal end of said tartar removal instrument.

10. A device as defined in claim 4, wherein said light source and said spectral reflectance detector comprise at least one optical fibre having distal sections located adjacent said distal end of said tartar removal instrument, and wherein said optical fibres comprise proximal sections that are detachably connected to said distal sections for allowing said distal sections and a working end of said tartar removal instrument to be selectively detached from said proximal sections for discarding said distal sections and said working end and replacing them with new ones, or for sterilising said distal sections and said working end before being returned to said proximal sections for further use thereof.

11. A device as defined in claim 4, wherein said light source and said spectral reflectance detector comprise at least one optical fibre having a distal end located adjacent said distal end of said tartar removal instrument and are independent from a working end of said tartar removal instrument, said working end being detachable from a handle of said tartar removal instrument such that said working end can be selectively detached for discarding said working end and replacing it with a new one, or for sterilising said working end before being returned to said handle for further use thereof.

12. A device as defined in claim 4, wherein said light source and said spectral reflectance detector comprise at least one optical fibre having a distal section located adjacent said distal end of said tartar removal instrument, said distal section being selectively displaceable along said working end such that a position of said distal section can be adjusted following wear of said working end.

13. A device as defined in claim 1, wherein said light source and said spectral reflectance detector each comprise proximal and distal sections that are detachably connected together for allowing said distal sections and a working end of said tartar removal instrument to be selectively detached from said proximal sections for discarding said distal sections and said working end and replacing them with new ones, or for sterilising said distal sections and said working end before being returned to said proximal sections for further use thereof, an optical connection member being provided between said proximal sections and said distal sections of said illumination and detection means.

14. A device as defined in claim 1, wherein there is provided an indicator means adapted to be actuated by said spectral reflectance detector to indicate to the operator the presence of tartar substantially at a position of a distal end of said detection means.

15. A device as defined in claim 14, wherein said indicator means comprises at least one of a luminous, a sound and a vibratory indicator.

16. A device as defined in claim 1, wherein said tartar removal instrument is at least one of power and manually actuated.

17. A device as defined in claim 1, wherein said second predetermined range of values cover wavelengths associated with spectral reflectance characteristics of said artefacts.

18. A device as defined in claim 1, wherein said analysing system comprises software for storing and/or updating data relative to a patient's history.

19. A device as claimed in claim 1 wherein said infrared range comprises wavelengths between 800 nm and 920 nm.

20. A device as claimed in claim 1, further comprising a second range of wavelengths that is appropriate for discriminating the spectral reflectance characteristics of tartar.

21. A device as claimed in claim 20 wherein said second range comprises wavelengths between 600 nm and 650 nm.

22. A device as claimed in claim 20 wherein said second range comprises wavelengths in the green region of the spectrum.

23. A device as claimed in claim 1 wherein said analyzing system produces a ratio of said values from said first and said second range of wavelengths.

24. A device as claimed in claim 1 wherein a working end of the tartar detection and removal device comprises a ceramic tip transparent to said wavelengths.

25. A device as claimed in claim 1, wherein said spectral reflectance detector operates under the lock-in detection principle.

* * * * *